United States Patent
Bucholz et al.

(10) Patent No.: US 6,236,875 B1
(45) Date of Patent: *May 22, 2001

(54) SURGICAL NAVIGATION SYSTEMS INCLUDING REFERENCE AND LOCALIZATION FRAMES

(75) Inventors: Richard D. Bucholz, St. Louis, MO (US); Kevin T. Foley, Memphis, TN (US); Kurt R. Smith, Boulder, CO (US); Daniel Bass, Moss Beach, CA (US); Thomas Wiedenmaier, San Carlos, CA (US); Todd Pope, San Francisco, CA (US); Udo Wiedenmaier, San Mateo, CA (US)

(73) Assignees: Surgical Navigation Technologies, Broomfield, CO (US); St. Louis University, St Louis, MO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/809,404
(22) PCT Filed: Oct. 5, 1995
(86) PCT No.: PCT/US95/12894
  § 371 Date: Jul. 23, 1997
  § 102(e) Date: Jul. 23, 1997
(87) PCT Pub. No.: WO96/11624
  PCT Pub. Date: Apr. 25, 1996

Related U.S. Application Data

(63) Continuation-in-part of application No. 08/319,615, filed on Oct. 7, 1994, now abandoned.
(60) Provisional application No. 60/003,415, filed on Sep. 8, 1995.

(51) Int. Cl.$^7$ .................................................. A61B 5/05
(52) U.S. Cl. ........................................ 600/407; 606/130
(58) Field of Search ................................ 600/407, 410, 600/414, 415, 417, 425, 426, 429, 437; 606/130

(56) References Cited

U.S. PATENT DOCUMENTS

| | | |
|---|---|---|
| D. 291,246 | 8/1987 | Lower . |
| D. 349,573 | 8/1994 | Bookwalter . |
| D. 353,668 | 12/1994 | Banks . |
| D. 357,534 | 4/1995 | Hayes . |
| D. 359,557 | 6/1995 | Hayes . |
| 3,821,469 | 6/1974 | Whetstone et al. . |
| 3,868,565 | 2/1975 | Kuipers . |
| 3,963,028 | 6/1976 | Cooley et al. . |
| 3,983,474 | 9/1976 | Kuipers ........................ 324/43 B |
| 4,058,114 | 11/1977 | Soldner . |
| 4,068,156 | 1/1978 | Johnson et al. . |
| 4,117,337 | 9/1978 | Staats . |
| 4,182,312 | 1/1980 | Mushabac ........................ 433/68 |
| 4,209,254 | 6/1980 | Reymond . |
| 4,259,725 | 3/1981 | Andrews et al. . |
| 4,341,200 | 7/1982 | Perry . |
| 4,341,220 | 7/1982 | Perry ........................ 606/130 |
| 4,358,856 | 11/1982 | Stivender et al. . |
| 4,368,556 | 1/1983 | Wanner et al. . |
| 4,396,945 | 8/1983 | DiMatteo et al. . |
| 4,398,540 | 8/1983 | Takemura et al. . |
| 4,407,298 | 10/1983 | Lentz et al. . |
| 4,419,012 | 12/1983 | Stephenson . |
| 4,457,311 | 7/1984 | Sorenson et al. . |
| 4,465,069 | 8/1984 | Barbier et al. . |
| 4,473,074 | 9/1984 | Vassiliadis . |
| 4,506,676 | 3/1985 | Duska . |
| 4,543,959 | 10/1985 | Sepponen . |
| 4,571,834 | 2/1986 | Fraiser et al. . |
| 4,583,538 | 4/1986 | Onic et al. . |
| 4,585,350 | 4/1986 | Pryer et al. . |
| 4,592,352 | 6/1986 | Patil . |
| 4,602,622 | 7/1986 | Bar et al. . |
| 4,608,977 | 9/1986 | Brown ........................ 128/303 B |
| 4,638,798 | 1/1987 | Sheldon et al. ............... 128/303 B |
| 4,649,504 | 3/1987 | Krouglicof et al. . |
| 4,651,732 | 3/1987 | Frederick . |
| 4,659,971 | 4/1987 | Suzuki et al. . |
| 4,660,970 | 4/1987 | Ferrano ........................ 356/1 |

| Patent No. | Date | Inventor | Class |
|---|---|---|---|
| 4,672,306 | 6/1987 | Thong . | |
| 4,673,352 | 6/1987 | Hansen . | |
| 4,674,057 | 6/1987 | Caughman et al. . | |
| 4,686,997 | 8/1987 | Oloff et al. . | |
| 4,698,777 | 10/1987 | Toyoda et al. . | |
| 4,701,047 | 10/1987 | Eibert et al. . | |
| 4,701,049 | 10/1987 | Beckmann et al. . | |
| 4,705,395 | 11/1987 | Hageniers . | |
| 4,705,401 | 11/1987 | Addleman | 356/376 |
| 4,706,665 | 11/1987 | Gouda | 128/303 B |
| 4,709,156 | 11/1987 | Murphy | 250/560 |
| 4,721,384 | 1/1988 | Dietrich et al. . | |
| 4,721,388 | 1/1988 | Takagi et al. . | |
| 4,722,056 | 1/1988 | Roberts et al. . | |
| 4,723,544 | 2/1988 | Moore et al. | 128/303 B |
| 4,727,565 | 2/1988 | Ericson . | |
| 4,733,661 | 3/1988 | Palestrant . | |
| 4,733,662 | 3/1988 | DeSatnick . | |
| 4,733,969 | 3/1988 | Case et al. | 356/375 |
| 4,737,032 | 4/1988 | Addleman et al. | 356/376 |
| 4,737,921 | 4/1988 | Goldwasser et al. . | |
| 4,742,815 | 5/1988 | Ninan et al. . | |
| 4,743,770 | 5/1988 | Lee | 250/560 |
| 4,743,771 | 5/1988 | Sacks et al. | 250/560 |
| 4,745,290 | 5/1988 | Frankel et al. | 250/560 |
| 4,750,487 | 6/1988 | Zanetti | 128/303 B |
| 4,753,128 | 6/1988 | Bartlett et al. . | |
| 4,753,528 | 6/1988 | Hines | 356/1 |
| 4,761,072 | 8/1988 | Pryor | 356/1 |
| 4,762,016 | 8/1988 | Stoughton et al. . | |
| 4,764,015 | 8/1988 | Bieringer et al. . | |
| 4,764,016 | 8/1988 | Johanasson | 356/371 |
| 4,767,934 | 8/1988 | Stauffer . | |
| 4,771,787 | 9/1988 | Wurster et al. . | |
| 4,775,235 | 10/1988 | Hecker et al. . | |
| 4,776,749 | 10/1988 | Wanzenberg et al. . | |
| 4,779,212 | 10/1988 | Levy | 364/562 |
| 4,782,239 | 11/1988 | Hirose et al. | 250/561 |
| 4,788,481 | 11/1988 | Niwa . | |
| 4,791,934 | 12/1988 | Brunnett | 606/130 |
| 4,793,355 | 12/1988 | Crum et al. . | |
| 4,794,262 | 12/1988 | Sato et al. | 250/560 |
| 4,803,645 | 2/1989 | Ohtomo et al. . | |
| 4,805,615 | 2/1989 | Carol . | |
| 4,809,694 | 3/1989 | Ferrara | 128/303 B |
| 4,821,200 | 4/1989 | Oberg | 364/474.24 |
| 4,821,206 | 4/1989 | Arora . | |
| 4,822,163 | 4/1989 | Schmidt | 356/1 |
| 4,825,091 | 4/1989 | Breyer et al. | 250/560 |
| 4,829,373 | 5/1989 | Leberl et al. | 358/88 |
| 4,835,710 | 5/1989 | Schnelle et al. . | |
| 4,836,778 | 6/1989 | Baumrind et al. | 433/69 |
| 4,837,669 | 6/1989 | Tharp et al. . | |
| 4,841,967 | 6/1989 | Chang et al. | 128/303 B |
| 4,875,478 | 10/1989 | Chen | 128/303 B |
| 4,896,673 | 1/1990 | Rose et al. . | |
| 4,931,056 | 6/1990 | Ghajar et al. | 606/653 R |
| 4,933,843 | 6/1990 | Scheller et al. . | |
| 4,943,296 | 7/1990 | Funakubo et al. . | |
| 4,945,914 | 8/1990 | Allen | 128/653 R |
| 4,955,891 | 9/1990 | Carol . | |
| 4,961,422 | 10/1990 | Marchosky . | |
| 4,982,188 | 1/1991 | Fodale et al. . | |
| 4,991,579 | 2/1991 | Allen | 128/653 R |
| 5,005,142 | 4/1991 | Lipchak et al. . | |
| 5,016,639 | 5/1991 | Allen | 128/653 R |
| 5,017,139 | 5/1991 | Mushabac | 433/109 |
| 5,027,818 | 7/1991 | Bova et al. | 128/653.1 |
| 5,039,867 | 8/1991 | Nishihara et al. . | |
| 5,047,036 | 9/1991 | Koutrouvelis . | |
| 5,050,608 | 9/1991 | Watanabe et al. . | |
| 5,059,789 | 10/1991 | Salcudean et al. . | |
| 5,078,140 | 1/1992 | Kwoh . | |
| 5,078,142 | 1/1992 | Siczek et al. . | |
| 5,079,699 | 1/1992 | Tuy et al. . | |
| 5,080,662 | 1/1992 | Paul . | |
| 5,086,401 | 2/1992 | Glassman et al. . | |
| 5,094,241 | 3/1992 | Allen | 128/653.1 |
| 5,097,839 | 3/1992 | Allan | 128/653.1 |
| 5,099,846 | 3/1992 | Hardy | 606/130 X |
| 5,107,839 | 4/1992 | Houdek et al. | 606/120 X |
| 5,119,817 | 6/1992 | Allen | 128/653.1 |
| 5,142,930 | 9/1992 | Allen et al. | 74/469 |
| 5,163,430 | 11/1992 | Carol . | |
| 5,178,164 | 1/1993 | Allen | 128/898 |
| 5,186,174 | 2/1993 | Schlondorff et al. . | |
| 5,193,106 | 3/1993 | DeSena . | |
| 5,197,476 | 3/1993 | Nowacki et al. . | |
| 5,198,877 | 3/1993 | Schulz . | |
| 5,207,223 | 5/1993 | Adler . | |
| 5,211,164 | 5/1993 | Allen | 128/653.1 |
| 5,222,499 | 6/1993 | Allen et al. . | |
| 5,224,049 | 6/1993 | Nushabac | 364/474.05 |
| 5,230,338 | 7/1993 | Allen et al. . | |
| 5,249,581 | 10/1993 | Horbal et al. . | |
| 5,251,127 | 10/1993 | Raab . | |
| 5,257,998 | 11/1993 | Ota et al. . | |
| 5,261,404 | 11/1993 | Mick et al. . | |
| 5,279,309 | 1/1994 | Taylor et al. . | |
| 5,291,889 | 3/1994 | Kenet et al. . | |
| 5,295,200 | 3/1994 | Boyer . | |
| 5,295,483 | 3/1994 | Nowacki et al. . | |
| 5,299,288 | 3/1994 | Glassman et al. . | |
| 5,305,091 | 4/1994 | Gelbart et al. . | |
| 5,305,203 | 4/1994 | Raab . | |
| 5,309,913 | 5/1994 | Kormos et al. . | |
| 5,355,129 | 10/1994 | Baumann . | |
| 5,357,953 | 10/1994 | Merrick et al. . | |
| 5,359,417 | 10/1994 | Muller et al. . | |
| 5,368,030 | 11/1994 | Zinreich et al. . | |
| 5,371,778 | 12/1994 | Yanof et al. . | |
| 5,383,454 | 1/1995 | Bucholz . | |
| 5,389,101 | 2/1995 | Heilbrum et al. . | |
| 5,391,199 | 2/1995 | Ben-Haim . | |
| 5,398,684 | 3/1995 | Hardy . | |
| 5,399,146 | 3/1995 | Nowacki et al. . | |
| 5,399,951 | 3/1995 | Lavallee et al. . | |
| 5,443,489 | 8/1995 | Ben-Haim . | |
| 5,447,154 | 9/1995 | Cinquin et al. . | |
| 5,480,422 | 1/1996 | Ben-Haim . | |
| 5,483,961 | 1/1996 | Kelly et al. . | |
| 5,490,196 | 2/1996 | Rudich et al. . | |
| 5,494,034 | 2/1996 | Schlondorff et al. . | |
| 5,515,160 | 5/1996 | Schulz et al. . | |
| 5,517,990 | 5/1996 | Kalfas et al. . | |
| 5,526,576 | 6/1996 | Fuchs et al. . | |
| 5,531,227 | 7/1996 | Schneider . | |
| 5,531,520 | 7/1996 | Grimson et al. . | |
| 5,546,951 | 8/1996 | Ben-Haim . | |
| 5,551,429 | 9/1996 | Fitzpatrick et al. . | |
| 5,558,091 | 9/1996 | Acker et al. . | |
| 5,568,809 | 10/1996 | Ben-Haim . | |
| 5,603,318 | 2/1997 | Heilbrum et al. . | |
| 5,617,857 | 4/1997 | Chader et al. . | |
| 5,622,170 * | 4/1997 | Schulz | 128/653.1 |
| 5,638,819 | 6/1997 | Manwaring et al. . | |
| 5,647,361 | 7/1997 | Damadian . | |
| 5,649,936 | 7/1997 | Real | 606/130 |
| 5,662,111 | 9/1997 | Cosman . | |
| 5,676,673 * | 10/1997 | Ferre et al. | 606/130 |
| 5,682,886 | 11/1997 | Delp et al. . | |
| 5,695,500 * | 12/1997 | Taylor et al. | 606/130 |

| | | | |
|---|---|---|---|
| 5,722,594 | * | 3/1998 | Barrick .................................. 600/407 |
| 5,732,703 | | 3/1998 | Kalfas et al. ...................... 128/653.1 |
| 5,755,725 | * | 5/1998 | Druais .................................. 606/130 |
| 5,769,861 | | 6/1998 | Vilsmeier ............................ 606/130 |
| 5,776,064 | | 7/1998 | Kalfas et al. ......................... 600/414 |
| 5,794,356 | | 8/1998 | Raab ....................................... 33/503 |
| 5,799,055 | * | 8/1998 | Peshkin et al. ......................... 378/42 |
| 5,836,954 | * | 11/1998 | Heilbrun et al. ..................... 606/130 |
| B1 5,383,454 | | 12/1996 | Bucholz . |

FOREIGN PATENT DOCUMENTS

| | | | |
|---|---|---|---|
| 2534516A1 | 2/1976 | (DE) . | |
| 2852949A | 6/1980 | (DE) . | |
| 3205085A1 | 9/1982 | (DE) . | |
| 3205915A1 | 9/1983 | (DE) . | |
| 3 508 730 A1 | 9/1986 | (DE) . | |
| 87 01 668 | 2/1987 | (DE) . | |
| 3717871 | 5/1987 | (DE) . | |
| 8701668 | 5/1987 | (DE) . | |
| 3838011 | 11/1988 | (DE) . | |
| 3904595 | 2/1989 | (DE) . | |
| 4233978 | 10/1992 | (DE) . | |
| 4432890A1 | 3/1996 | (DE) . | |
| 0 018 166 | 10/1980 | (EP) . | |
| 0 062 941 | 10/1982 | (EP) | .............................. A61B/5/10 |
| 0 155 857 | 1/1985 | (EP) . | |
| 0 207 452 | 1/1987 | (EP) . | |
| 0 322 363 | 6/1989 | (EP) . | |
| 0 326 768 | 8/1989 | (EP) . | |
| 0 359 773 | 3/1990 | (EP) . | |
| 0 427 358 | 5/1991 | (EP) . | |
| 0 456 103 | 11/1991 | (EP) . | |
| 0 469 966 | 2/1992 | (EP) . | |
| 0 581 704 | 2/1994 | (EP) . | |
| 0 603 089 | 6/1994 | (EP) . | |
| 0 501 993 | 5/1996 | (EP) . | |
| 2 417 970 | 10/1979 | (FR) . | |
| 2 094 590 | 9/1982 | (GB) . | |
| 62-000327 | 1/1987 | (JP) . | |
| WO 88/09151 | 12/1988 | (WO) . | |
| WO 90/05494 | 5/1990 | (WO) . | |
| WO 91/04711 | 4/1991 | (WO) . | |
| WO 91/07726 | 5/1991 | (WO) . | |
| WO92/00702 | 1/1992 | (WO) . | |
| WO 92/06645 | 4/1992 | (WO) . | |
| WO 93/10710 | 6/1993 | (WO) . | |
| WO 93/2052 | 10/1993 | (WO) . | |
| WO 94/06352 | 3/1994 | (WO) . | |
| WO 94/23647 | 10/1994 | (WO) . | |
| WO 94/24933 | 11/1994 | (WO) . | |
| WO 95/11624 | 5/1995 | (WO) . | |
| WO 96/11624 | 4/1996 | (WO) . | |

OTHER PUBLICATIONS

Ohbuchi, R. et al., Incremental volume reconstruction and rendering for 3D ultrasound imaging, Visualization in Biomedical Computing, SPIE vol. 1808, pp. 312–323, 1992.

L. Adams et al., "Aide Au Reperage Tridimensionnel Pour La Chirugie De La Base Du Crane," Innov. Tech. Biol. Med., vol. 13, No. 4, pp. 329–341, 1992.

Ludwig Adams et al., "Medical Imaging: Computer–Assisted Surgery," *IEEE Computer Graphics and Applications*, pp. 43–51, May 1990.

Eric E. Awwad et al.,"MR Imaging of Lumbar Juxtaarticular Cysts," *Journal of Computer Assisted Tomography*, vol. 14 No. 3, pp. 415–417, May/Jun. 1990.

Eric E. Awwad et al., "Post–Traumatic Spinal Synovial Cyst with Spondylolysis CT Features," *Journal of Computer Assisted Tomography*, vol. 13, No. 2, pp. 334–337, Mar./Apr. 1989.

Yukio Kosugi et al., "An Articulated Neurosurgical Navigation System Using MRI and CT Images," *IEEE Transactions on Biomedical Engineering*, vol. 35, No. 2, pp. 147–152, Feb. 1988.

Ralph Mösges et al., "A New Imaging Method for Intraoperative Therapy Control in Skull–Base Surgery," *Neurosurg.*, Rev. 11, pp. 245–247, 1988.

David W. Roberts, M.D., et al., "A Frameless Stereotaxic Integration of Computerized Tomographic Imaging and the Operating Microscope,"*J. Neurosurg.*, vol. 65, pp. 545–549, Oct. 1986.

M. Peter Heilbrun, M.D., "Computed Tomography–Guided Stereotactic Systems," *Clinical Neurosurgery*, pp. 564–580, 1983.

Alexander R. MacKay, M.D., et al., "Computed Tomography–Directed Stereotaxy for Biopsy and Interstitial Irradiation of Brain Tumors: Technical Note," *Neurosurgery*, vol. II, No. 1, Part I, pp. 38–42, 1982.

Michael L.J. Apuzzo, et al., "Computed Tomographic Guidance Stereotaxis in the Management of Intracranial Mass Lesions," *Neurosurgery*, vol. 12, No. 3, pp. 277–285, 1983.

Neil B. Horner, M.D., et al., "A Comparison of CT–Stereotaxic Brain Biopsy Techniques," *Investigative Radiology*, vol. 19, pp. 367–373, Apr. 12, 1984.

André Olivier et al., "Frameless stereotaxy for surgery of the epilepsies: preliminary experience" *J. Neurosurg.*, vol. 81, No. 4, pp. 629–633, Oct. 1994.

Howard A. Paul et al., "Development of a Surgical Robot for Cementless Total Hip Arthroplasty," *Clinical Orthopaedics*, No. 285, p. 57–66, Dec. 1992.

C.A. Pelizzari et al., "Interactive 3D Patient–Image Registration" *Information Procession in Medical Imaging*, Proceedings, pp. 132–141, Jul. 1991.

Richard D. Penn et al., "Stereotactic Surgery with Image Processing of Computerized Tomographics Scans," *Neurosurgery*, vol. 3, No. 2, pp. 157–163, May 26, 1978.

Claude Picard et al., "The First Human Stereotaxic Apparatus" *J. Neurosurg.*, vol. 59, pp. 673–676, Oct. 1983.

PixSys Inc, "Real–Time Image–Guided Surgery and Planning, FlashPoint 3D Localizer," *Investigational Device Brochure*, 3 pages (unnumbered and undated).

H. F. Reinhardt et al., "Surgery of Brain Neoplasms Using 32–P Tumour Marker," *Acta Neurochir*, vol. 97, pp. 89–94, 1989.

H. F. Reinhardt et al., "CT–Guided 'Real Time' Stereotaxy," *Acta Neurochirurgica Suppl.*, vol. 46, pp. 107–108, 1989.

H. F. Reinhardt et al., "Interactive Sonar–Operated Device for Stereotactic and Open Surgery," *Stereotac Funct Neurosurg*, vols. 54 and 55, pp. 393–397, Oct. 1989.

H. F. Reinhardt et al., "Mikrochirurgische Entfernung tiefliegender GefaBmiBbildungen mit Hilfe der sonar–Stereometrie," *Ultraschall in Med. 12*, pp. 80–84, 1991.

H. F. Reinhardt et al., "Neuronavigation: A Ten–Year Review," Neurosurgery, vol. 23, pp. 329–341 (1992).

Hans F. Reinhardt et al., "Sonic Stereometry in Microsurgical Procedures for Deep–Seated Brain Tumors and Vascular Malformations," *Neurosurgery*, vol. 32, No. 1, pp. 329–341, Jan. 1993.

Pixsys, Inc., "Alignment Procedure for the Pixsys Two–Emitter Offset Probe for the SAC GP–8–3d Sonic Digitizer" (undated), 3 unnumbered pages.

Pixsys, Inc., "Pixsys: 3–D Digitizing Accessories," Aug. 1989, 6 unnumbered pages.

Arun–Angelo Patil, M.D., "Computed Tomography Plane of the Target Approach in Computed Tomographic Stereotaxis," *Neurosurgery*, vol. 15, No. 3, pp. 410–414, 1984.

Lauri V. Laitinen, M.D., "Trigeminus Stereoguide: An Instrument for Stereotactic Approach Through the Foramen Ovale and Foramen Jugulare," *Surg. Neurol.*, vol. 22, pp–519–525, 1984.

D.E. Bullard, et al., "CT–Guided Stereotactic Biopsies Using a Modified Frame and Gildenberg Techniques," *J. of Neurology, Neurosurgery and Psychiatry*, vol. 47, pp. 590–595, Jan. 5, 1984.

J.M. Van Buren, et al., "A Multipurpose CT–Guided Stereotactic Instrument of Simple Design," *Proc. Of the American Soc. Stereotactic and Functional Neurology*, vol. 46, pp. 211–216, 1983.

Pixsys, Inc., "Design Aide," Mar. 1989, 5 unnumbered pages.

"3–D Digitizer Captures the World," *BYTE Magazine*, Oct. 1990, p. 43.

H. Reinhardt, et al., "A Computer Assisted Device for the Intraoperative CT–Correlated Localization of Brain Tumors," *Eur. Surg. Res.*, vol. 20, pp. 52–58, 1988.

Eric H. Friets, et al., "A Frameless Stereotaxic Operating Microscope for Neurosurgery," *IEEE Transactions on Biomedical Engineering*, vol. 36, No. 6, Jun. 1989.

Eiju Watanabe, M.D., et al., "Three–Dimensional Digitizer," (Neuronavigator): New Equipment for Computed Tomography–Guided Stereotaxic Surgery, *Surg. Neurol.*, vol. 27, pp. 543–547, 1987.

Pixsys, Inc., "SACDAC User's Guide, Version 2e," Mar. 1989, pp. 0–1 through 5–3.

Pixsys, Inc., "Offset Probe for Science Accessories' GP–8–3d Digitizer," Dec. 2, 1987, one page.

Patrick J. Kelly, M.D., et al., "Computer–Assisted Stereotaxic Laser Resection of Intra–Axial Brain Neoplasma," *J. of Neurosurg.*, vol. 64, pp. 427–439, Mar. 1986.

Pascal Sautot, et al., "Computer Assisted Spine Surgery: a First Step Toward Clinical Application in Orthopaedics," *14th IEEE EMBS*, pp. 1071–1072, 1992.

Christine S. Siegel, "Creating 3D Models from Medical Images Using AVS," Research Paper, N.Y.U. School of Medicine, 4 pages.

D.A. Simon, et al., "Accuracy Validation in Image–Guided Orthopaedic Surgery," Research Paper, Canegie Mellon University and Shadyside Hospital, pp. 185–192.

Kurt R. Smith et al., "The Neurostation TM—A Highly Accurate, Minimally Invasive Solution to Frameless Stereotactic Neurosurgery," *Computerized Medical Imaging and Graphics*, vol. 18, No. 4, pp. 247–256, 1994.

Kurt R. Smith et al., "Multimodality Image Analysis and Display Methods for Improved Tumor Localization in Stereotactic Neurosurgery," *Annual Conference of the IEEE Engineering in Medicine and Biology Society*, vol. 13, No. 1, pp. 0210, 1991.

Kurt R. Smith, et al., "Computer Methods for Improved Diagnostic Image Display Applied to Stereotactic Neurosurgery," *Automedica*, vol. 14, pp. 371–382, 1992.

Spencer et al., "Unilateral Transplanation of Human Fetal Mesencephalic Tissue into the Caudate Nucleus of Patients with Parkinson's Disease" *The New England Journal of Medicine*, vol. 327, No. 22, pp. 1541–1548, Nov. 26, 1992.

Watanabe, "Neuronavigator," *Iqaku–no–Ayumi*, vol. 137, No. 6, 4 pages, May 10, 1986 (with translation).

Afshar, Farhad, et al., "A three–dimensional reconstruction of the human brain stem," *J. Neurosurg.*, vol. 57, Oct. 1982, pp. 491–495.

Bajcsy, Ruzena, et al., "Computerized Anatomy Atlas of the Human Brain," Proceedings of the Second Annual Conference & Exhibition of The National Computer Graphics Association, Inc., Jun. 14–18, 1981, pp. 435–441.

Batnitzky, Solomon, M.D., et al., "Three–Dimensional Computer Reconstructions of Brain Lesions from Surface Contours Provided by Computed Tomography: A Prospectus," *Neurosurgery*, vol. 11, No. 1, 1982, pp. 73–84.

Bergström, Mats, et al., "Stereotaxic Computer Tomography," *Am. J. Roentgenol*, 127:167–170, 1976, pp. 167–170.

Birg, W., et al., "A Computer Programme System for Stereotactic Neurosurgery," *Acta Neurochirurgica Suppl.*, 24, 1977, 99–108.

Boëthius, J., et al., "Stereotactic Biopsies and Computer Tomography in Gliomas," *Acta Neurochirurgica*, vol. 40, Fasc. 3–4, 1978, pp. 223–232.

Boëthius, J., et al., "Stereotaxic computerized tomography with a GE 8800 scanner," *J. Neurosurg*, vol. 52, 1980, pp. 794–800.

Brown, Russell A., M.D., "A computerized tomography–computer graphics approach to stereotaxic localization," *J. Neurosurg*, vol. 50, 1979, pp. 715–720.

Edward C. Benzel et al., "Magnetic Source Imaging: A Review of the Magnes System of Biomagnetic Technologies Incorporated," *Neurosurgery*, vol. 33, No. 2, pp. 252–259, Aug. 1993.

Russell A. Brown, "A Stereotactic Head Frame for Use with CT Body Scanners," *Inv. Radiol.*, vol. 14, No. 4, pp. 300–304, Jul. 1979.

Richard D. Bucholz et al., "A Comparison of Sonic Digitizers Versus Light Emitting Diode–Based Localization," *Interactive Image–Guided Neurosurgery*, Chapter 16, pp 179–200.

Bucholz, R.D., et al., "Use of an Intraoperative Optical Digitizer in a System for Free–Hand Stereotactic Surgery," Poster #1120, *Scientific Program*, 1992 Annual Meeting, American Association of Neurological Surgeons, San Francisco, CA, Apr. 11–16, 1992, pp. 284–285.

Richard D. Bucholz et al., "Image–Guided Surgical Techniques for Infections and Trauma of the Central Nervous System," *Neurosurgery Clinics of North America*, vol. 7, No. 2, pp. 187–200, Apr. 1996.

Richard D. Bucholz et al., "Intraoperative Localization Using a Three Dimensional Optical Digitizer," *Proceedings of Clinical Applications of Modern Imaging Technology*, vol. 1894, The International Society of Optical Engineering, pp. 312–322, Jan. 17–19, 1993.

Richard D. Bucholz et al., "Variables Affecting the Accuracy of Stereotactic Localization Using Computerized Tomography," *J. Neurosurg.*, vol. 79, pp. 667–673, Nov. 1993.

Richard D. Bucholz, "The Central Sulcus and Surgical Planning," *AJNR*, vol. 14, pp. 926–927, Jul./Aug. 1993.

Richard D. Bucholz et al., "Halo Vest Versus Spinal Fusion for cervical injury: evidence from an outcome study," *J. Neurosurg.*, vol. 70, No. 6, pp. 884–892, Jun. 1989.

Richard D. Bucholz, "Intraoperative Ultrasonic Brain Shift Monitor and Analysis," St. Louis University Hospital.

Guillaume Champleboux, "Utilisation De Fonctions Splines Pour La Mise Au Point d'Un Capteur Tridimensionnel Sans Contact," Jul. 1991.

Gayle Hanson, "Robots Roll into Operating Rooms," *INSIGHT*, Apr. 8, 1991, pp. 44–45.

G. Champleboux, et al., "Accurate Calibration of Cameras and Range Imaging Sensors: the NPBS Method," IEEE Conference on Robotics and Automation, 1992.

P. Cinquin et al., "Computer Assisted Medical Interventions," *IARP*, p. 63–65, Sep. 1989.

Philippe Cinquin et al., "IGOR: Image Guided Robot. Methodology, Applications," *IEEE EMBS*, pp. 1–2, 1992.

Patrick Clarysse et al., "A Computer–Assisted System for 3–D Frameless Localization in Stereotaxic MRI," *IEEE TOMA*, vol. 10, No. 4, pp. 523–529, Dec. 1991.

C. A. Pelizzari et al., "Interactive 3D Patient," Lecture notes in Computer Science 12th International Conference, pp. 136–141, Jul. 1991.

Bill Dever and S. James Zinreich, M.D., "OR role seen for 3–D imaging," *Radiology Today*, 2 pages, Feb. 1991.

Jocelyne Troccaz et al., "The Use of Localizers, Robots and Synergistic Devices in CAS.".

Kevin T. Foley et al, "Image–Guided Intraoperative Spinal Localization," *Intraoperative Neuroprotection*, Chapter 19, pp. 325–340, 1996.

Christopher C. Gallen et al., "Intracranial Neurosurgery Guided by Functional Imaging," *Surg. Neurol.*, vol. 42, pp. 523–530, Jan. 3, 1994.

Robert L. Galloway, Jr., et al.,"Interactive Image–Guided Neurosurgery," *IEEE TOMA*, vol. 39, No. 12, pp. 1228–1231, Dec. 1992.

Edmund M. Glaser et al., "The Image–Combining Computer Microscope–an Interactive Instrument for Morphometry of the Nerous System," *Journal of Neuroscience Methods*, vol. 8, pp. 17–32, 1983.

John G. Golfinos et al., "Clinical Use of a Frameless Stereotaxic Arm: results of 325 cases," *J. Neurosurg.*, vol. 83, No. 3, pp. 197–205, Aug. 1995.

Camilo R. Gomez et al., "Transcranial Doppler Ultrasound Following Closed Head Injury: Vasospasm or Vasoparalysis?," *Surg. Neurol.*, vol. 35, No. 1, pp. 30–35, Jan. 1991.

J.F. Hatch et al., "Reference–Display System for the Integration of CT Scanning and the Operating Microscope," Proceedings of the Eleventh Annual Northeast Bioengineering Conference, pp. 252–254, Mar. 15, 1985.

M. Peter Heilburn et al., "Preliminary Experience with a Brown–Roberts–Wells (BRW) Computerized Tomography Stereotaxic Guidance System," *J. Neurosurg.*, vol. 59, pp. 217–222, Aug. 1983.

Jaime M. Henderson et al., "An Accurate and Ergonomic Method of Registration for Image–Guided Neurosurgery," Computerized Medical Imaging and Graphics, vol. 18, No. 4, pp. 273–277, 1994.

Skip Jacques et al., "A Computerized Microstereotactic Method to Approach, 3–Dimensionally Reconstruct, Remove and Adjuvantly Treat Small CNS Lesions," *Appl. Neurophysiol.*, vol. 43, pp. 176–182, 1980.

Amami Kato, M.D., et al., "A Frameless, Armless Navigational System for Computer–Assisted Neurosurgery," *J. Neurosurg.*, vol. 74, pp. 845–849, May 1991.

Patrick J. Kelly, "Instrumentation, Technique and Technology," *Neurosurgery*, vol. 37, No. 2, pp. 348–350, Aug. 1995.

Ludger Klimek et al., "Long–Term Experience with Different Types of Localization Systems in Skull–Base Surgery," *Ear, Nose and Throat Surgery*, vol. 51, pp. 635–638, 1993.

Douglas Kondziolka et al., "Guided Neurosurgery Using the ISG Viewing Wand," *Contemporary Neurosurgery*, vol. 17, No. 8, pp. 1–6, 1995.

Krybus et al., "Navigation Support for Surgery by Means of Optical Position Detection," Lehrstuhl fur MeBbtechnik.

S. Lavallee, "A New System for Computer Assisted Neurosurgery," IEEE Engineering in Medicine & Biology Society 11th Annual International Conference, 2 pages, 1989.

Stephane Lavallee, "Vi Adaptation De La Methdologie A Quelques Applications Cliniques," Lère Partie: Methdologie des GMCAO, Chapter VI, pp. 133–148.

S. Lavallee, et al, "Computer Assisted Driving of a Needle into the Brain," CAR, p. 416–20, 1989.

S. Lavallee et al., "Computer Assisted Interventionist Imaging: The Instance of Stereotactic Brain Surgery," MEDINFO, pp. 613–617, 1989.

Stéphane Lavallée et al., "Computer Assisted Medical Interventions," NATO ASI Series, vol. F60, p. 302–12, 1990.

S. Lavallee et al., "Computer Assisted Puncture," Afcet, Tome 1, pp. 439–449 Nov. 1987.

S. Lavallee et al., "Matching of Medical Images for Computed and Robot Assisted Surgery" 1991.

Michael L. Levy et al., "Heads–up Intraoperative Endoscopic Imaging: A Prospective Evaluation of Techniques and Limitations," *Neurosurgery*, vol. 40, No. 3, pp. 526–529, Mar. 1997.

J. F. Mallet, M.D., et al., "Post–Laminectomy Cervical–Thoracic Kyphosis in a Patient with Von Recklinghausen's Disease," *Spinal Frontiers*, vol. 3, Issue 1, Apr. 1996.

Mazier et al., "Chirurgie De La Colonne Vertebrale Assiste Par Ordinateur: Application Au Vissage Pediculaire," *Innov. Tech. Biol. Med.*, vol. 11, No. 5, pp. 559–566, 1990.

B. Mazier et al., "Computer Assisted Interventionist Imaging: Application to Vertebral Column Surgery," Annual International Conference of the IEEE Engineering in Medicine and Biology Society, vol. 12, No. 1, pp. 0430–0431, 1990.

Mazier et al., "Computer Assisted Vertebral Column Surgery: Application to the Spinal Pedicle Fixation," Innov. Tech. Biol. Med., vol. 11/5, 1990, p.

F. Mesqui et al., "Real–Time, Noninvasive Recording and Three–Dimensional Display of the Functional Movements of an Arbitrary Mandible Point," *SPIE Biostereometrics '85*, vol. 602, pp. 77–84, Dec. 3–6, 1985.

Klaus Obergfell et al., "Vision Sensing for Control of Long–Reach Flexible Manipulators," Research Paper, Georgia Institute of Technology, 6 pages.

Klaus Obergfell et al., "End–Point Position Measurements of Long–Reach Flexible Manipulators," Research Paper, Georgia Institute of Technology, 6 pages.

Gildenberg, Philip L., M.D., et al., "Calculation of Stereotactic Coordinates from the Computed Tomographic Scan," *Neurosurgery*, vol. 10, No. 5, 1982, pp. 580–586.

Gleason, Curtis A., Ph.D., et al., "Stereotactic Localization (with Computerized Tomographic Scanning), Biopsy, and Radiofrequency Treatment of Deep Brain Lesions," *Neurosurgery*, vol. 2, No. 3, 1978, pp. 217–222.

Gouda, Kasim I., M.D., et al., "New frame for sterotaxic surgery," *J. Neurosurg*, vol. 53, 1980, pp. 256–259.

Greitz, T., et al., "Head Fixation System for Integration of Radiodiagnostic and Therapeutic Procedures," *Neuroradiology*, vol. 19, No. 1, 1980, pp. 1–6.

Hahn, Joseph F., M.D., et al., "Needle Biopsy of Intracranial Lesions Guided by Computerized Tomography," *Neurosurgery*, vol. 5, No. 1, 1979, pp. 11–15.

Hinck, Vincent C., M.D., et al., "A precise technique for craniotomy localization using computerized tomography," *J. Neurosurg*, vol. 54, Mar. 1981, pp. 416–418.

Hoerenz, Peter, "The Operating Microscope, I., Optical Principles, Illumination Systems, and Support Systems," *Journal of Microsurgery*, vol. 1, Mar.–Apr. 1980, pp. 364–369.

Hounsfield, G.N., Computerized transverse axial scanning (tomography): Part 1., Description of System, *British Journal of Radiology*, vol. 46, 1973, pp. 1016–1022.

Jacques, Skip, M.D., et al., "Computerized three–dimensional stereotaxic removal of small central nervous system lesions in patients," *J. Neurosurg*, vol. 53, Dec. 1980, pp. 816–820.

Kaufman, Howard H., M.D., "New Head–positioning System for Use with Computed Tomographic Scanning," *Neurosurgery*, vol. 7, No. 2, 1980, pp. 147–149.

Leksell, L., et al., "Stereotaxis and Tomography, A Technical Note," *Acta Neurochirurgica*, vol. 52, Fasc–12, 1980, pp. 1–7.

Levinthal, Robert, M.D., et al., "Technique for Accurate Localization with the CT Scanner," *Bulletin of the Los Angeles Neurological Societies*, vol. 41, No. 1, Jan. 1976, pp. 6–8.

Lunsford, L. Dade, M.D., "Innovations in Stereotactic Technique Coupled with Computerized Tomography," *Contemporary Neurosurgery*, 1982, pp. 1–6.

MacKay, Alexander R., M.D., et al., "Computed Tomography–directed Stereotaxy for Biopsy and Interstitial Irradiation of Brain Tumors: Technical Note," *Neurosurgery*, vol. 11, No. 1, Jul. 1982, pp. 38–42.

Maroon, Joseph C., M.D., et al., "Intracranial biopsy assisted by computerized tomography," *J. Neurosurg.*, vol. 46, No. 6, Jun. 1977, pp. 740–744.

Moran, Christopher J., M.D., et al., "Central Nervous System Lesions Biopsied or Treated by CT–Guided Needle Placement," *Radiology*, vol. 131, No. 3, Jun. 1979, pp. 681–686.

Mundinger, F., et al., "Computer–Assisted Stereotactic Brain Operations by Means Including Computerized Axial Tomography," *Applied Neurophysiology*, vol. 41, Nos. 1–4, 1978, pp. 169–182.

Mundinger, F., et al., "Treatment of Small Cerebral Gliomas with CT–Aided Stereotaxic Curietherapy," *Neuroradiology*, vol. 16, Jun. 4–10, 1978, pp. 564–567.

Norman, David, M.D., et al., "Localization with the EMI Scanner," *The American Journal of Roentgenology, Radium Therapy and Nuclear Medicine*, vol. 125, No. 4, Dec. 1975, pp. 961–964.

O'Leary, Daniel H., M.D., et al., "Localization of vertex lesions seen on CT scan," *J. Neurosurg*, vol. 49, No. 1, Jul. 1978, pp. 71–74.

Perry, John H., Ph.D., et al., "Computed Tomography–guided Stereotactic Surgery: Conception and Development of a New Stereotactic Methodology," *Neurosurgery*, vol. 7, No. 4, Oct. 1980, pp. 376–381.

Piskun, Walter S., Major, et al., "A Simplified Method of CT Assisted Localization and Biopsy of Intracranial Lesions," *Surgical Neurology*, vol. II, Jan.–Jun. 1979, pp. 413–417.

Rosenbaum, Arthur E., et al., "Computerized Tomography Guided Stereotaxis: A New Approach," *Applied Neurophysiology*, vol. 43, Nos. 3–5, Jun. 4–7, 1980, pp. 172–173.

Scarabin, J.M., et al., "Stereotaxic Exploration in 200 Supratentorial Brain Tumors," *Neuroradiology*, vol. 16, Jun. 4–10, 1978, pp. 591–593.

Yeates, Andrew, M.D., et al., "Simplified and accurate CT–guided needle biopsy of central nervous system lesions," *Journal of Neurosurgery*, vol. 57, No. 3, Sep. 1982, pp. 390–393.

Patrick J. Kelly, et al., "Stereotactic CT Scanning for the Biopsy of Intracranial Lesions and Functional Neurosurgery," *Applied Nurophysiology*, Dec. 1983, Karger, AG, Basel, pp. 193–199.

C. Hunter Shelden, M.D., et al., "Development of a computerized microstereotaxic method for localization and removal of minute CNS lesions under direct 3–D vision," *J. Neurosurg*, vol. 52, Jan. 1980, pp. 21–27.

Skip Jacques, M.D., et al., "Computerized three–dimensional stereotaxic removal of small central nervous system lesions in patients," *J. Neurosurg*, vol. 53, No. 6, Dec. 1980, pp. 816–820.

P.J. Kelly, et al., "Precision Resection of Intra–Axial CNS Lesions by CT–Based Stereotactic Craniotomy and Computer Monitored $CO_2$ Laser," *Acta Neurochirurgica*, Springer–Verlag 1983, vol. 68, 1983, pp. 1–9.

Dean Schulz, Ph.D, President, PixSys, "Offset Probe for SAC GP8–3d digitizer," information flyer, not dated.

SAC Science Accessories Corporation, Technical Bulletin, "Model GP–8 Sonic Digitizer," "Mark II Sonic Digitizer (Model GP–7 Grafbar)," "3–Dimensional Sonic Digitizer (Model GP–8–3D)," U.S.A., 6 pages, not numbered, not dated.

Patrick J. Kelly, M..D., et al. "A Microstereotactic Approach to Deep–seated Arteriovenous Malformations," *Surgical Neurology*, vol. 17, No. 4, Apr. 1982, pp. 260–262.

S. Lavalee, et al., "Matching 3–D Smooth Surfaces with their 2–d Projections using 3–D Distance Maps," SPIE, vol. 1570, 1991, pp. 322–336.

Y.C. Shiu, et al., "Finding the Mounting Position of a Sensor by Solving a Homogeneous Transform Equation of Form AX=XB," *IEEE*, 1987, pp. 1666–1671.

K.S. Arun et al., "Transactions on Pattern Analysis and Machine Intelligence," *IEEE*, vol. PAMI–9, No. 5, 1987, pp. 698–770.

James M. Balter, et al., "Correlation of projection radiographs in radiation therapy using open curve segments and points," *Med. Phys.* 19 (2), Mar./Apr. 1992, pp. 329–334.

B. Leonard Holman, et al., Computer–Assisted Superimposition of Magnetic Resonance and High–Resolution Technetium–99–m–HMPAO and Thallium–201 SPECT Images of the Brain, *The Journal of Nuclear Medicine*, vol. 32, No. 8, Aug. 1991, pp. 1478–1484.

C.A. Pelizzari, et al., 3D Patient/Image Registration: Application to Radiation Treatment Planning, *Medical Physics*, vol. 18, No. 3, May/Jun. 1991, p. 612.

D.J. Valentino, et al., Three–Dimensional Visualization of Human Brain Structure–Function Relationships, *The Journal of Nuclear Medicine*, Oct. 1989, Posterboard 1136, vol. 30, No. 10, p. 1747.

David N. Levin, et al., "The Brain: Integrated Three–dimensional Display of MR and PET Images," *Radiology,* Sep. 1989, vol. 172, No. 3, pp. 783–789.

Charles A. Pelizzari, et al., "Accurate Three–Dimensional Registration of CT, PET and/or MR Images of the Brain," *Journal of Computer Assisted Tomography,* 13(1):20–26, Jan./Feb. 1989, Raven Press, pp. 20–26.

C.A. Pelizzari, et al., "Interactive 3D Patient–Image Registration," *Lecture Notes in Computer Science,* Springer–Verlag, Wye, UK, 1991 Proceedings, pp. 132–141.

D. Levin, et al., "Multimodality 3–D View of the Brain Created from MRI and PET Scans," *SMRI 1989: Seventh Annual Meeting Program and Abstracts,* vol. 7, Supplement 1, p. 89.

C.A. Pelizzari, et al., "Three Dimensional Correlation of PET, CT and MRI Images," *The Journal of Nuclear Medicine,* Abstract Book, 34th Annual Meeting, Toronto, Canada, 1987, vol. 28, No. 4, Poster Session No. 528, p. 682.

John F. Hatch, "Reference–Display System for the Integration of CT Scanning and the Operating Microscope," Trustees of Dartmouth College, Oct. 1984, entire thesis.

Patrick J. Kelly, M.D., et al., "A Stereotactic Approach to Deep–Seated Central Nervous System Neoplasms Using the Carbon Dioxide Laser," *Surgical Neurology,* vol. 15, No. 5, May 1981, pp. 331–334.

* cited by examiner

*Primary Examiner*—William E. Kamm
*Assistant Examiner*—Eleni Mantis Merlader
(74) *Attorney, Agent, or Firm*—Finnegan, Henderson, Farabow, Garrett & Dunner, L.L.P.

(57) ABSTRACT

A system for use during a medical or surgical procedure on a body. The system generates an image representing the position one or more body elements during the procedure using scans generated by a scanner prior or during the procedure. The image data set has reference points for each of the body elements, the reference points of a particular body element having a fixed spatial relation to the particular body element. The system includes an apparatus for identifying, during the procedure, the relative position of each of the reference points of each of the body elements to be displayed. The system also includes a processor for modifying the image data set according to the identified relative position of each of the reference points during the procedure, as identified by the identifying apparatus, said processor generating a displaced image data set representing the position of the body elements during the procedure. The system also includes a display utilizing the displaced image data set generated by the processor, illustrating the relative position of the body elements during the procedure. Methods relating to the system are also disclosed. Also disclosed are devices for use with a surgical navigation system having a sensor array which is in communication with the device to identify its position. The device may be a reference frame for attachment of a body part of the patient, such as a cranial reference arc frame for attachment to the head on a spine reference arc frame for attachment to the spine. The device may also be a localization frame for positioning an instrument relative to a body part, such as a localization biopsy guide frame for positioning a biopsy needle, a localization drill guide assembly for positioning a drill bit, a localization drill yoke assembly for positioning a drill, or a ventriculostomy probe for positioning a catheter.

46 Claims, 22 Drawing Sheets

POSITION IN SURGERY
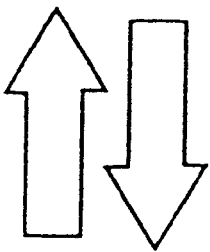
REGISTRATION
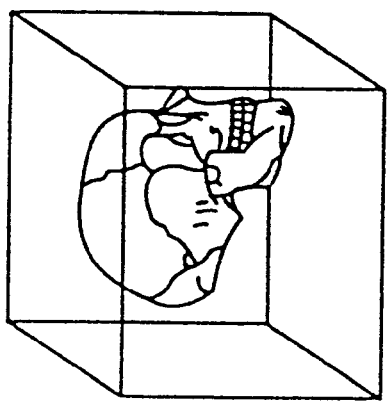
PRE-SURGICAL SCANS (IMAGE DATASET)
FIG. 1
PRIOR ART

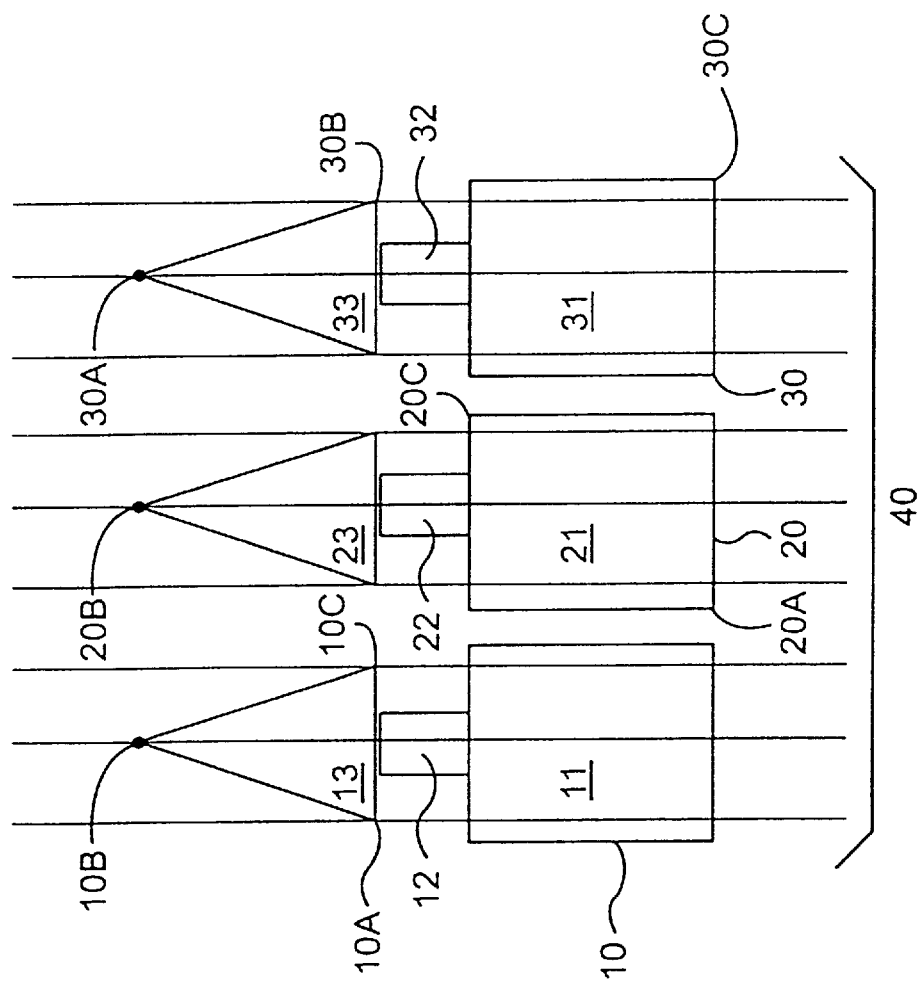

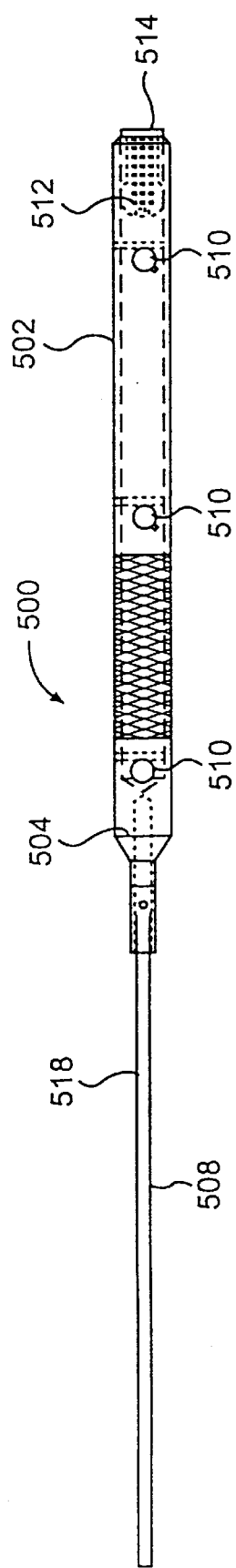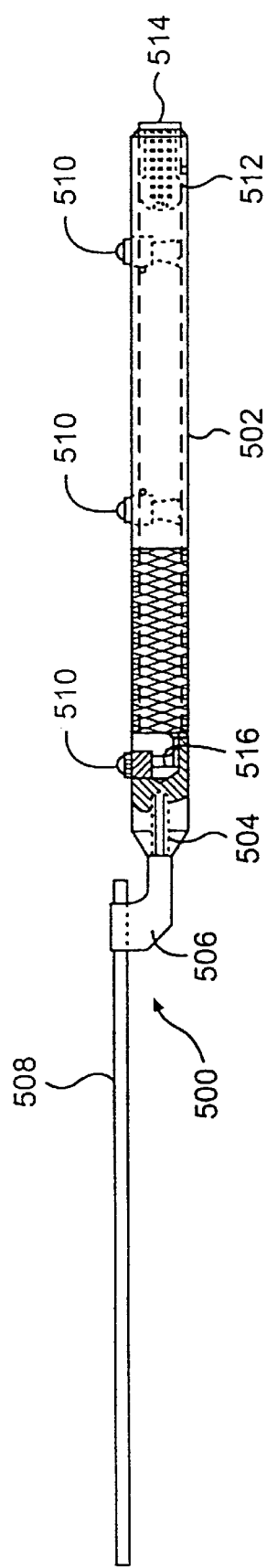
FIG. 13H
FIG. 13I

United States Patent

SURGICAL NAVIGATION SYSTEMS INCLUDING REFERENCE AND LOCALIZATION FRAMES

CROSS REFERENCE TO RELATED APPLICATIONS

This application is a continuation-in-part of U.S. patent application Ser. No. 08/319,615, filed Oct. 7, 1994, which has been abandoned. This application claims priority to U.S. Provisional Patent Application Ser. No. 60/003,415, filed Sep. 8, 1995. In addition, the disclosure of U.S. patent application Ser. No. 08/524,981, issued as U.S. Pat. No. 5,871,445, is incorporated by reference herein in its entirety.

BACKGROUND OF THE INVENTION

The invention relates generally to systems which use and generate images during medical and surgical procedures, which images assist in executing the procedures and indicate the relative position of various body parts and instruments. In particular, the invention relates to a system for generating images during medical and surgical procedures based on a scan taken prior to or during the procedure and based on the present position of the body parts and instruments during the procedure.

Image guided medical and surgical procedures comprise a technology by which scans, obtained either pre-procedurally or intra-procedurally (i.e., prior to or during a medical or surgical procedure), are used to generate images to guide a doctor during the procedure. The recent increase in interest in this field is a direct result of the recent advances in scanning technology, especially in devices using computers to generate three dimensional images of parts of the body, such as computed tomography (CT) or magnetic resonance imaging (MRI).

The majority of the advances in diagrammatic imaging involve devices which tend to be large, encircle the body part being imaged, and are expensive. Although the scans produced by these devices depict the body part under investigation with high resolution and good spatial fidelity, their cost usually precludes the dedication of a unit to be used during the performance of procedures. Therefore, image guided surgery is usually performed using images taken preoperatively.

The reliance upon preoperative images has focused image guidance largely to the cranium. The skull, by encasing the brain, serves as a rigid body which largely inhibits changes in anatomy between imaging and surgery. The skull also provides a relatively easy point of reference to which fiducials or a reference system may be attached so that registration of pre-procedural images to the procedural work space can be done simply at the beginning, during, or throughout the procedure. Registration is defined as the process of relating pre-procedural or intra-procedural scan of the anatomy undergoing surgery to the surgical or medical position of the corresponding anatomy. For example, see Ser. No. 07/909,097, now U.S. Pat. No. 5,383,454 the entire disclosure of which is incorporated herein by reference.

This situation of rigid fixation and absence of anatomical movement between imaging and surgery is unique to the skull and intracranial contents and permits a simple one-to-one registration process as shown in FIG. 1. The position during a medical procedure or surgery is in registration with the pre-procedural image data set because of the absence of anatomical movement from the time of the scan until the time of the procedure; in effect, the skull and it's intracranial contents comprise a "rigid body," that is, an object which does not deform internally. In almost every other part of the body there is ample opportunity for movement within the anatomy which degrades the fidelity by which the pre-procedural scans depict the intra-procedural anatomy. Therefore, additional innovations are needed to bring image guidance to the rest of the body beyond the cranium.

The accuracy of image guided surgery relies upon the ability to generate images during medical and surgical procedures based on scans taken prior to or during the procedure and based on the present position and shape of the body parts during the procedure. Two types of body parts are addressed herein: 1) structures within the body that do not change shape, do not compress, nor deform between the process of imaging and the medical procedure, which are termed "rigid bodies," and are exemplified by the bones of the skeleton; and 2) structures within the body that can change shape and deform between the process of imaging and the medical procedure structures are termed "semi-rigid bodies," and are exemplified by the liver or prostate. Both types of body parts are likely targets for medical or surgical procedures either for repair, fusion, resection, biopsy, or radiation treatment. Therefore, a technique is needed whereby registration can be performed between the body parts as depicted pre-procedurally on scans and the position and shape of these same body parts as detected intra-procedurally. This technique must take into account that movement can occur between portions of the body which are not rigidly joined, such as bones connected by a joint, or fragments of a broken bone, and that shape deformation can occur for semi-rigid bodies, such as the liver or prostate. In particular, the technique must be able to modify the scanned image dataset such that the modified image dataset which is used for localization and display, corresponds to position and/or shape of the body part(s) of interest during a medical or surgical procedure. A key to achieving this correspondence is the ability to precisely detect and track the position and/or shape of the body part(s) of interest during the medical or surgical procedure, as well as to track instruments, ------- or radiation used during the said procedure.

SUMMARY OF THE INVENTION

It is an object of this invention to provide a system which allows registration between a body part depicted in pre-procedural images and tracked during surgery.

It is a further object of this invention to provide a system which allows registration between a semi-rigid body such as the liver depicted in pre-procedural images and detected during surgery.

It is a further object of this invention to provide a system which allows registration between multiple body parts such as skeletal elements depicted in pre-procedural images and detected during surgery.

It is a further object of this invention to provide a system which can localize a semi-rigid body that may deform between imaging and a procedure and provide a display during the procedure of the body in its deformed shape.

It is a further object of this invention to provide a system which can localize multiple rigid bodies that move with respect to each other between imaging and a procedure and provide a display during the procedure of the bodies in their displaced positions.

It is another object of this invention to provide a system for use during a medical or surgical procedure on the body, the system generating a display representing the position of one or more body elements during the procedure based on a scan generated by a scanner either prior to or during the procedure.

It is another object of this invention to provide a system for use during a medical or surgical procedure on a body which modifies the scan taken prior to or during a procedure according to the identified relative position of each of the elements during the procedure.

It is another object of this invention to provide a system for use during a medical or surgical procedure on a body which modifies the image data set according to the identified shape of each of the element during the procedure.

It is another object of this invention to provide a system which generates a display representative of the position of a medical or surgical instrument in relation to the body element(s) during a procedure.

It is a further object of this invention to provide a system for use during image guided medical and surgical procedures which is easily employed by the doctor or surgeon conducting the procedure.

It is another object of this invention to provide a system which determines the relative position and/or shape of body elements during a medical or surgical procedure based on the contour of the body elements which can avoid the need for exposing the body elements.

It is still another object of this invention to provide a system which employs one or more two dimensional fluoroscopic or x-ray images of body elements to determine their relative position and/or shape in three dimensions.

It is yet a further object of this invention to describe a surgical or medical procedure which employs a display representing the position of the body element(s) during the procedure based on an image data set of the body element(s) generated prior to the procedure.

It is a further object of this invention to provide a system and method for medical or surgical procedures which allows repositioning of body elements during the procedure and still permits the generation of a image showing the relative position of the body elements.

It is a further object of this invention to provide a system and method for medical or surgical procedures which allows reshaping of the body element(s) during the procedure and still permits the generation of a image showing the position and current shape of the body elements.

It is a further object of this invention to provide a system which can localize a body element and provide a display during the procedure of the position of the body element relative to an instrument, such as a forceps, microscope, or laser, so that the instrument can be precisely located relative to the body element.

Other objects and features will be in part apparent and in part pointed out hereinafter.

The invention comprises a system for use during a medical or surgical procedure on a patient's body. The system generates one or more images representing the position and shape of one or more body elements during the procedure using scans generated by a scanner prior to the procedure, the scans having at least one reference point for each of the body elements of interest. These two dimensional scans, taken together, comprise a three dimensional depiction of the body, and are called the image data set. The reference points of a particular body element have a spatial relation to the particular body element. The system includes means for identifying, during the surgical or medical procedure, the position of the reference points of each of the body elements to be displayed by the system. The system also includes a means processor for modifying the image data set according to the identified position of the reference points of each of the body elements during the medical or surgical procedure, called the identifying means. The processor generates images using a modified (displaced and/or deformed) image data set representing the position and shape of the body elements during the procedure. Optionally, the processor determines the position of a medical or surgical instrument relative to these body elements. The system also includes a display which utilizes the modified image data set generated by the processor to illustrate the position and shape of the body elements during the procedure and optionally the determined position of the medical or surgical instrument relative to the body elements by means of two dimensional images.

The invention also comprises a method for use during a procedure. The method generates images representing the position and shape of one or more body elements during the procedure based on scans generated prior to the procedure, which scan set has reference points for each of the body elements. The method comprises the steps of:

identifying, during the procedure, the position of the reference points of each of the body elements to be displayed;

modifying the image data set according to the identified position of the reference points of each body element during the procedure in order to generate a modified (displaced and/or deformed) image data set representing the position of the body elements during the procedure;

optionally determining the position of a medical or surgical instrument, probe or beam of irradiation relative to the body elements; and generating a display based on the modified image data set illustrating the position and shape of the body elements during the procedure and optionally the position of the medical or surgical instrument relative to the body elements.

The invention also comprises a method for use with two or more body elements each of which have reference points. Prior to the procedure, the method comprises the steps of placing the body elements in a frame to fix their relative position; and scanning the fixed body elements. During the procedure, the method comprises the steps of:

placing the body elements in the frame so that the body elements have the same relative position as their position during scanning;

determining the position of reference points on the body elements relative to reference means;

determining the position of a medical or surgical instrument relative to the reference means;

determining the position of the medical or surgical instrument relative to the body elements; and generating a display based on the pre-procedural scanning illustrating the determined position of the medical or surgical instrument relative to the body elements.

The invention also comprises a device for use with a surgical navigation system having a sensor array which is in communication with the device to identify its position, the device for use in guiding a catheter, the device for engaging a cable connected to the surgical navigation system, the cable for providing signals for activating the device. A handle has a cavity therein. A plurality of light emitting diodes on the handle emit light, when activated, for communicating with the sensor array of the surgical navigation system. A connector attached to the handle and adapted to engage the cable connected to the surgical navigation system receives the signals for activating the diodes. Wires located in the cavity of the handle and electrically interconnecting the connector and the light emitting diodes transmit the signals received by the connector to the diodes. A guide member connected to the handle guides the catheter.

The invention also comprises a device for use with a surgical navigation system having a sensor array which is in communication with the device to identify its position. A base member has a cavity therein. A plurality of light emitting diodes on the base member emit light, when activated, for communicating with the sensor array of the surgical navigation system. An activating circuit connected to the diodes provides signals for activating the diodes. Wires located in the cavity of the base member and electrically interconnecting the power supply and the light emitting diodes transmit the signals for activating the diodes.

The invention also comprises a device for use with a surgical navigation system having a sensor array which is in communication with the device to identify its position, the device for engaging a structure attached to or an instrument in known relation to a body part thereby providing a known reference relative to the body part, the device having a connector for engaging a cable connected to the surgical navigation system, the cable for providing signals for activating the device. A base member has a cavity therein. A coupling on the base member engages the structure in order to maintain the base member in fixed relation to the body part thereby providing the fixed reference. A plurality of light emitting diodes on the base member, said diodes, when activated, emitting light for communicating with the sensor array of the surgical navigation system. A connector attached to the base member and adapted to engage the cable connected to the surgical navigation system receives the signals for activating the diodes. Wires located in the cavity of the base member and electrically interconnecting the connector and the light emitting diodes transmit the signals received by the connector to the diodes to activate the diodes.

The invention also comprises a device for use with a surgical navigation system having a sensor array which is in communication with the device to identify its position, the device for guiding an instrument for engaging a body part thereby locating the instrument at a known position relative to the body part, the device having a connector for engaging a cable connected to the surgical navigation system, the cable for providing signals for activating the device. A housing has a cavity therein. A structure on the housing guides the instrument in order to maintain the instrument in a relationship relative to the housing. A plurality of light emitting diodes on the housing, when activated, emit light for communicating with the sensor array of the surgical navigation system. A connector attached to the housing and adapted to engage the cable connected to the surgical navigation system receives the signals for activating the diodes. Wires located in the cavity of the housing and electrically interconnecting the connector and the light emitting diodes and for transmitting the signals received by the connector to the diodes to activate the diodes.

In addition, the invention comprises a surgical navigation system comprising:
 a controller;
 a sensor array;
 a reference frame in communication with the array to identify its position; and
 a localization frame in communication with the array to identify a position of the localization frame, the localization frame for guiding the instrument for engaging the body part thereby locating the instrument at a known position relative to the body part, the localization frame connected to the controller which provides signals for activating the localization frame.

BRIEF DESCRIPTION OF THE DRAWINGS

FIG. 1 is an illustration of the prior art system in which rigid fixation and absence of movement between imaging and surgery permits a one-to-one registration process between the pre-surgical scan and the position in surgery.

FIG. 3 is an illustration of the pre-procedural alignment of three body elements during scanning.

FIG. 13H is a top plan view of one preferred embodiment of a ventriculostomy probe including an integrated localization frame according to the invention.

FIG. 13I is a side plan view, partially in cross section, of one preferred embodiment of a ventriculostomy probe including an integral localization frame according to the invention.

Corresponding reference characters indicate corresponding parts throughout the drawings.

DETAILED DESCRIPTION OF THE PREFERRED EMBODIMENTS

Figure 2A:
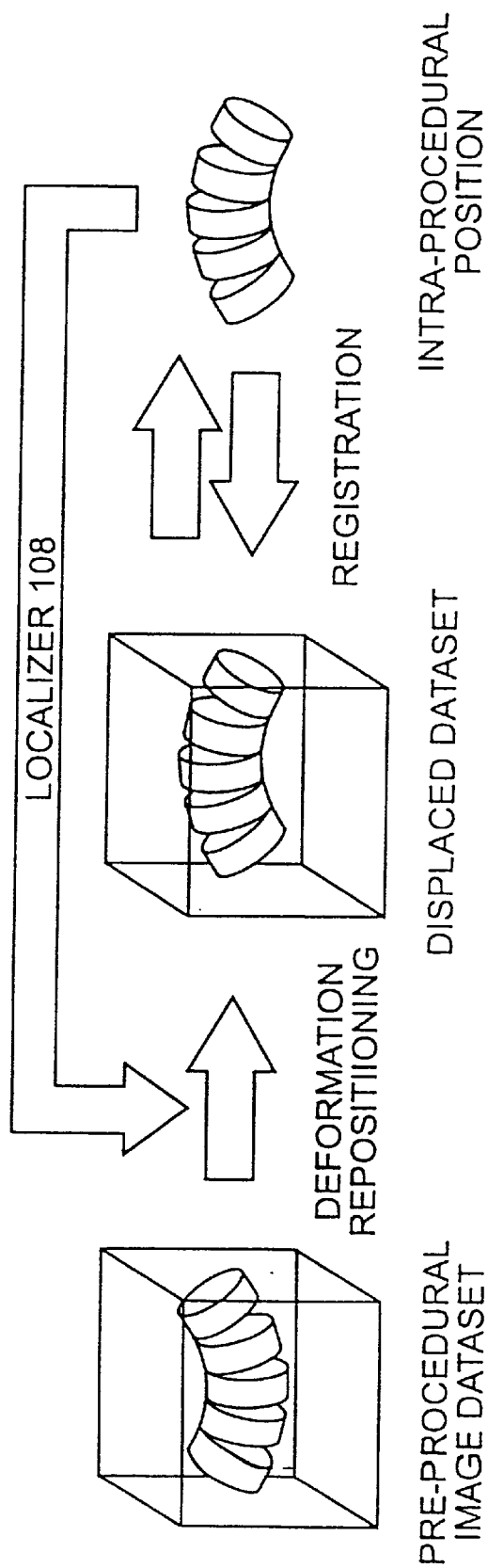
FIG. 2A is an illustration of operation of the invention in which the pre-procedural image data set is modified in accordance with the intra-procedural position in order to generate a displaced and/or deformed data set representative of the intra-procedural position.
Figure 2B:
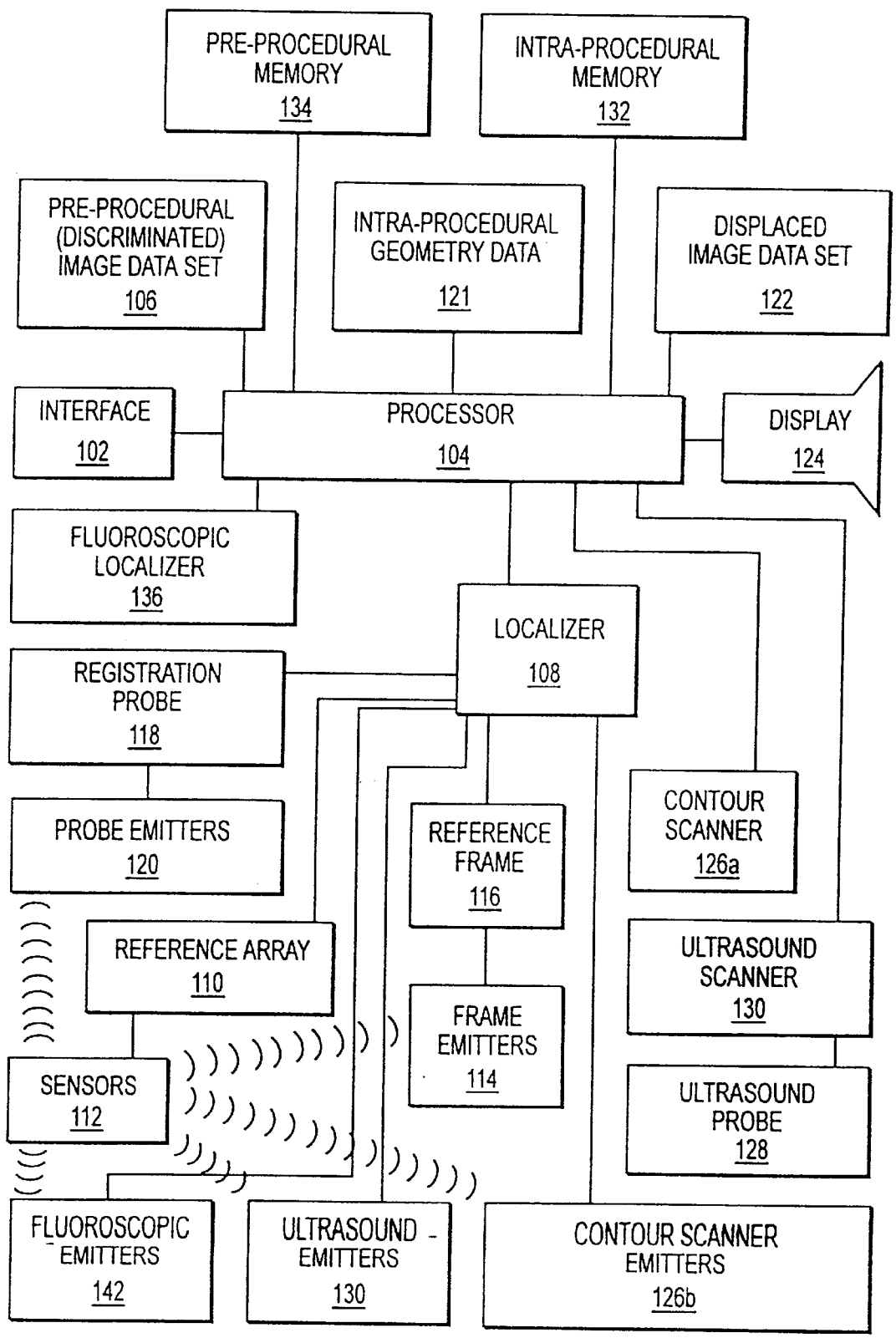
FIG. 2B is a block diagram of one preferred embodiment of a system according to the invention.

Referring to FIGS. 2A and 2B, an overview of operation of one preferred embodiment of the system according to the invention is illustrated. Prior to a particular procedure, the body elements which will be part of the procedure are scanned to determine their alignment, i.e., their pre-operative position. For example, the alignment may be such as illustrated in FIG. 3 wherein body elements 10, 20, and 30 are more or less aligned in parallel. These body elements may be bones or other rigid bodies. In FIG. 3, three-dimensional skeletal elements 10, 20, 30 are depicted in two dimensions as highly stylized vertebral bodies, with square vertebra 11, 21, 31, small rectangular pedicles 12, 22, 32, and triangular spinous processes 13, 23, 33. During imaging, scans are taken at intervals through the body parts 10, 20, 30 as represented in FIG. 3 by nine straight lines generally referred to be reference character 40. At least one scan must be obtained through each of the body elements and the scans taken together constitute a three-dimensional pre-procedural image data set.

FIG. 2B is a block diagram of the system according to the invention. A scanner interface 102 allows a processor 104 to obtain the pre-procedural image data set generated by the scanner and store the data set in pre-procedural image data set memory 106. Preferably, after imaging, processor 104 applies a discrimination process to the pre-procedural image data set so that only the body elements 10, 20, 30 remain in memory 106. If a discrimination process is employed, processor 104 may execute the discrimination process while data is being transferred from the scanner through the scanner interface 102 for storage in memory 106. Alternatively, memory 106 may be used for storing undiscriminated data and a separate memory (not shown) may be provided for storing the discriminated data. In this alternative, processor 104 would transfer the data set from the scanner through scanner interface 102 into memory 106 and then would discriminate the data stored in memory 106 to generate a discriminated image data set which would be stored in the separate memory.

Once the body elements 10, 20, 30 are discriminated and each defined as a single rigid body, they can be repositioned by established software algorithms to form the displaced image data set. Each rigid body element, 10, 20, 30, must have at least three recognizable reference points which are visible on the pre-procedural images. These reference points must be accurately detected during the procedure. For body part 10, reference points 10A, 10B, and 10C are located on the spinous process 13; for body part 20, reference points 20A and 20C are located on the vertebra 21 and reference point 20B is located on spinous process 23; and for body part 30, reference points 30A and 30B are located on the spinous process 33 and reference point 30C is located on the vertebra 31. More than one reference point can be selected on each scan through the bone, although the maximal accuracy of registration is achieved by separating the reference points as far as possible. For example, in the case of posterior spinal surgery, it may be preferable to select reference points 10A, 10B, and 10C on the spinous process which is routinely exposed during such surgery. It is contemplated that system software may allow the manual or automated identification of theme same points on the images of the body elements 10, 20, 30. As FIG. 3 is a two-dimensional projection of a three-dimension process, the reference points will not be limited to a perfect sagittal plane, as depicted.

After imaging, the skeletal body elements 10, 20, 30 may move with respect to each other at the joints or fracture lines. In the procedure room, such as an operating room or a room where a medical procedure will be performed, after positioning the patient for surgery, the body elements will assume a different geometry, such as the geometry depicted in FIG. 4.

Figure 4:
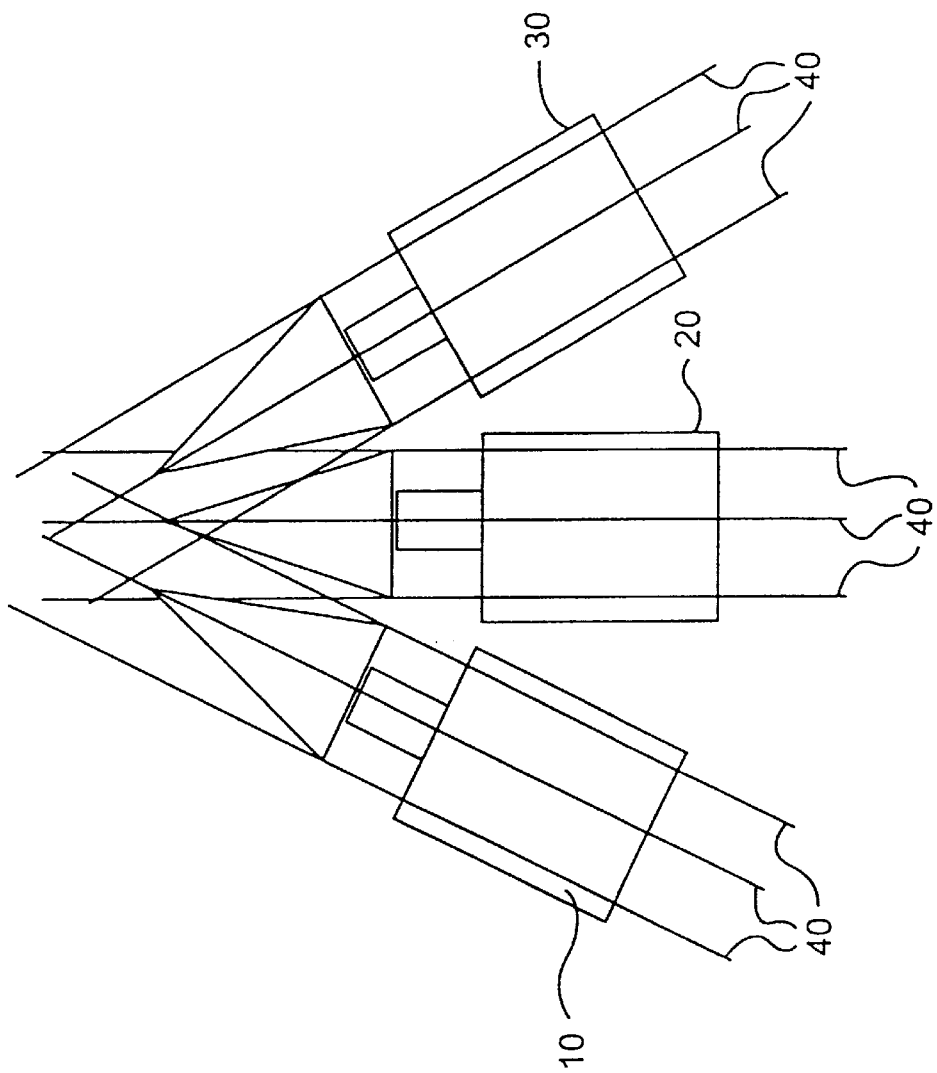
FIG. 4 is an illustration of the intra-procedural alignment of the three body elements of FIG. 3 during surgery.
Figure 5:
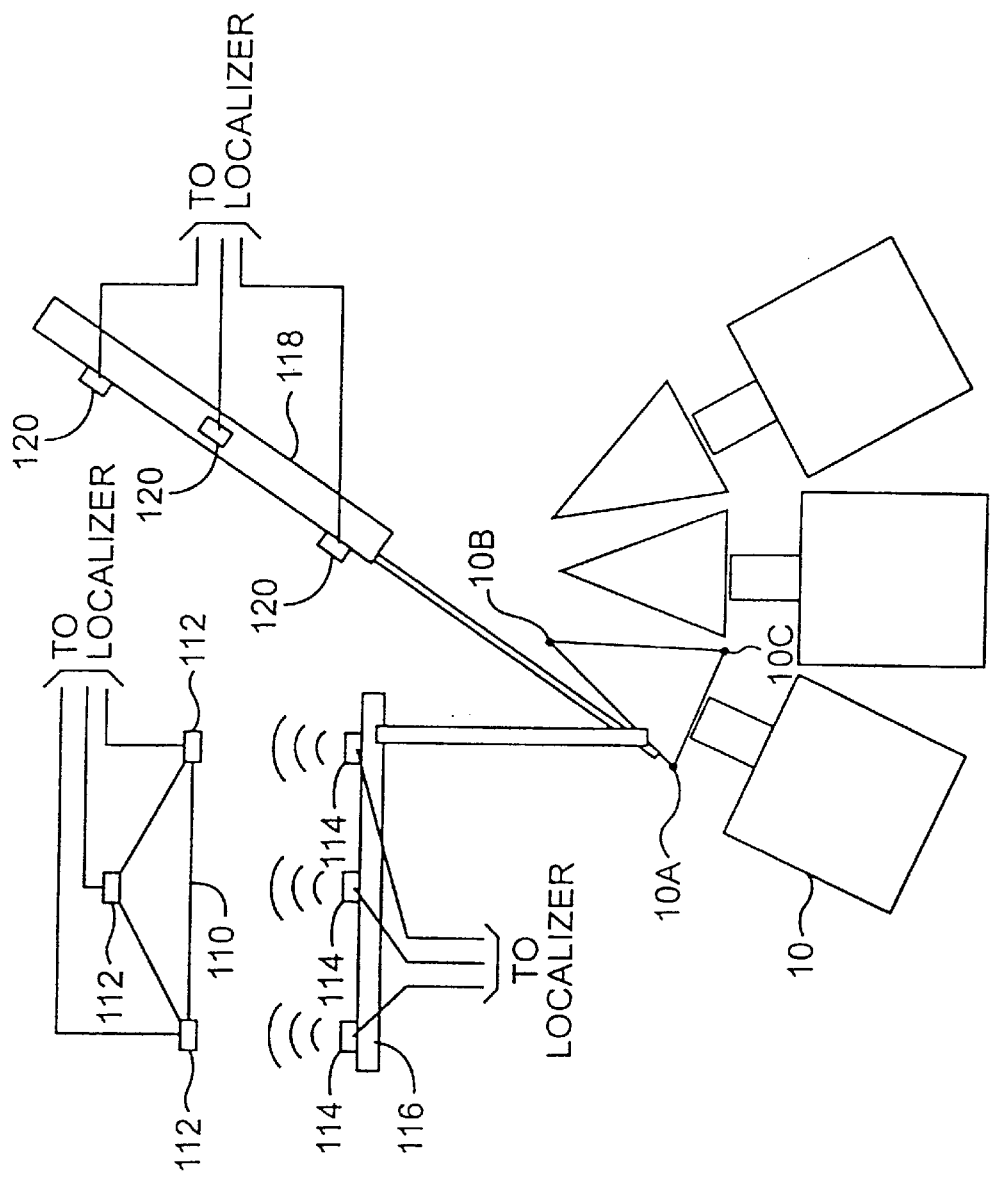
FIG. 5 is an illustration of three body elements, one of which has a reference frame attached thereto, in combination with a registration probe.

As a result of this movement, the pre-procedural image data set stored in memory 106, consisting of the scans through the skeletal elements, does not depict the operative position of the skeletal elements, as shown in FIG. 4. However, the shape of the skeletal elements, as depicted by the scans through the element, is consistent between imaging and procedure since they are rigid bodies, as indicated by the lines 40 through each element in FIG. 4. Therefore, the image data set must be modified to depict the intra-procedural geometry of the skeletal elements. This modification is performed by identifying the location of each reference point of each skeletal element in procedure space. As diagrammatically illustrated in FIGS. 2A and 2B, a localizer 108 (see FIG. 13, below, for more details) identifies the location and provides this information so that the pre-procedural data set may be deformed or re-positioned into the displaced data set. As a result, the displaced data set is in registration with the intra-procedural position of the elements 10, 20, 30. Once the locations of the reference points are determined by the localizer 108, processor 104, which is a part of the work station, can execute software which re-positions the images of the skeletal elements to reflect the position of the actual elements in the procedure room thus forming the displaced set and the registration between the displaced set and the intra-procedural position.

Preferably, a three-dimensional digitizer may be used as the localizer 108 to determine the position and space of the elements 10, 20, 30 during the procedure. In general, the digitizer would include a reference array 110 which receives emissions from a series of emitters. Usually, the emissions consist of some sort of energy, such as light, sound or electromagnetic radiation. The reference array 110 is distant from the emitters which are applied to and positioned in coordination with the elements being localized, determining the position of the emitters. As is apparent, the emitters may be placed distant to the elements and the reference array 110 may be attached to the elements being localized.

Referring to FIGS. 2A and 2B, an alternate preferred embodiment of the system according to the invention in the case where the body elements are not rigid, but rather semi-rigid such that shape deformations may occur to the body elements is described as follows. Prior to a particular procedure, the body elements which will be part of the procedure are scanned to determine their pre-operative position and shape. For example, the alignment may be such as illustrated in FIG. 3 wherein body elements 10, 20, and 30 are more or less aligned in parallel and have a defined shape. These body elements may be soft tissue such as the prostate or other semi-rigid bodies.

After imaging, the elements 10, 20, 30 may move with respect to each other and also their shape may become deformed. In the procedure room, such as an operating room or a room where a medical procedure will be performed, after positioning the patient for surgery, the body elements may assume a different geometry, such as the geometry depicted in FIG. 4 where geometry depicts both element alignment (position) and shape.

As a result of thin changed geometry, the pre-procedural image data set stored in memory 106, does not depict the operative geometry of the body elements, as shown in FIG. 4. Indeed, the shape of the body elements, as depicted by the scans through the element, may have changed between imaging and procedure since they are semi-rigid bodies. Therefore, the image data set must be modified to depict the current geometry of the body elements. This modification is performed by identifying the location of the reference points of each body element in procedure space. As diagrammatically illustrated in FIG. 2B, a localizer 108, possibly in communication with a processor 104, identifies the location of the reference points and provides this information so that the pre-procedural data set may be deformed into the displaced data set. Once the locations of the reference points are determined, processor 104, which is a part of the work station, can execute software which modifies the images of the body elements to reflect the geometry of the actual elements in the procedure room thus forming the displaced set and the registration between the displaced set and the intra-procedural position. As a result, the displaced data set is in registration with the intra-procedural geometry of the elements 10, 20, 30.

According to one preferred embodiment of the invention, a reference frame 116 is attached to one of the body elements 10 at the beginning of the procedure. Various reference frame embodiments are illustrated in more detail in FIGS. 11A–11C and 12A–12G below. Reference frame 116 is equipped with a plurality of emitters 114 which together define a three-diensional intraprocedural coordinate system with respect to the body element 10. In conventional terms, the reference frame 116 defines the stereotactic space with respect to the body element 10. Emitters 114 communicate with sensors 112 on a reference array 110 located in the procedure room and remote from the reference frame 116 and patient. If the body of the patient is not immobilized during surgery, then multiple reference frames may be required for each body element to define a surgical space with respect to each element. The surgical space may alternatively be defined by rigid fixation of the frame emitters 114 directly (or indirectly, for example, to the skin) to the skeletal elements 10, 20, or 30. In either case, the emitters 114 emit a signal which is received by the sensors 112. The received signal is digitized to compute position, for example, by triangulation. Through such information, the localizer 108 or a digitizer which is part of the localizer 108 can determine the exact three-dimensional position of the frame emitters 114 relative to the sensors 112. Thereby, localizer 108 or the processor 104 can exactly determine the position of the reference frame 116 relative to the array which is free to move except during localization, e.g., activation of the emitters 114 on the reference frame 116 and activation of the probe emitters 112. Emitters 114 of the reference frame 116 are energized to provide radiation to the sensors 112, which radiation is received and generates signals provided to the localizer 108 for determining the position of the frame 116 relative to the array 110.

Next, it is necessary to determine the position of the body element 10, which may be a skeletal element, to which the reference frame 116 is affixed or positioned with respect to. In particular, the position of the body element 10 relative to the reference frame 116 must be determined, thereby determining the position of the body element 10 in the surgical space defined by the reference frame 116. After exposure of the reference points 10A, 10B, 10C by surgical dissection, the reference points are touched by the tip of a registration probe 118 equipped with emitters 120. As each of the reference points 10A, 10B, 10C is touched by the tip of the probe 120, the emitters are energized to communicate with the sensors 112 of reference array 110. This communication permits the localizer 108 to determine the position of the registration probe 120, thereby determining the position of the tip of the probe 120, thereby determining the position of the reference point 10A on which the tip is positioned. By touching each of the reference-points 10A, 10B, 10C on each body element 10, 20, 30 involved in the procedure, an intra-procedural geometry data is generated and stored in memory 121. This data is related to the corresponding reference points on the pre-procedural images of the same elements by processor 104 which employs software to derive a transformation which allows the determination of the exact procedural position, orientation, and shape in surgical space of each body element, and thereby modifies the pre-procedural image data set stored in memory 106 to produce a displaced image data set which is stored in memory 122. The displaced image data set in memory 122 reflects the geometry of the actual elements 10, 20, 30 during the procedure. Processor 104 displays the displaced image data set on display 124 to provide a visual depiction of the geometry of the body elements 10, 20, 30 during the procedure. This image is used during the procedure to assist in the procedure. In addition, it is contemplated that an instrument, such as a forceps, a laser, a microscope, an endoscope, or a radiation delivery system, which would be used during the procedure, may be modified by the addition of emitters. This modified device when moved into the area of the body elements 10, 20, 30 would be activated so that its emitters would communicate with the reference array 110 thereby permitting localizer 108 to determine the instrument's position. As a result, processor 104 would modify display 124 to indicate the position of the instrument or the instruments focal point, such as by positioning a cursor, with respect to the body elements 10, 20, 30.

Further, it is contemplated that the addition of emitters on an instrument (effect or) may be used with the system in order to create a closed-loop feedback for actively (in the case of robotics) or passively controlling or monitoring the instrument and its position. Such a control loop allows the monitoring of certain procedures such as the delivery of radiation to the body or the use of a drill where the object of the procedure is to keep the focal point of the instrument in a safe zone, i.e. a predetermined procedural plan. Such a control loop could also control the operation of a robotically controlled instrument where the robotics could be driven (directly or indirectly) by processor 104 to control the position the position of the instrument. For example, the processor could instruct a robotic arm to control the position of a laser. The laser position could be monitored, such as by emitters on the laser. The processor would be programmed with the control parameters for the laser so that it would precisely follow a predetermined path.

Reference frame 116 allows the patient to be moved during the procedure without the need for re-registering the position of each of the body elements 10, 20, 30. It is assumed that during the procedure, the body elements are fixed relative to each other. Since the reference frame 116 is fixed (directly or indirectly) to body element 10, movement of the patient results in corresponding movement of the reference frame 116. Periodically, or after each movement of the patient, array, emitters 114 may be energized to communicate with the sensors 112 of reference array 110 in order to permit localizer 108 to determine the position of the reference frame 116. Since the reference frame 116 is in a known relative position to element 110 and since we have assumed that elements 20 and 30 are in fixed relation to element 10, localizer 108 and/or processor 104 can determine the position of the elements and thereby maintain registration.

An alternative to touching the reference points A, B, C with the tip of the probe 118 would be to use a contour scanner 126a with emitters attached 126b. Such a device, using some form of energy such as sound or light which is emitted, reflected by the contour and sensed, would allow the extraction of a contour of the body elements 10, 20, 30, thus serving as a multitude of reference points which would allow registration to occur. The registration process is analogous to the process described for ultrasound extracted contours below.

In certain situations, markers may be used on the skin surface as reference points to allow the transformation of the pre-procedural image data set into the displaced image data set. Reciprocally, skin surface fiducials applied at the time of imaging can be used to re-position the body to match the geometry during imaging and is described below.

Localization of body elements 10, 20, 30 may be desired without intra-procedural exposure of the reference points A, B, C on those body elements. Examples wherein the spine is minimally exposed include percutaneous biopsy of the spine or discectomy, spinal fixation, endoscopy, percutaneous spinal implant insertion, percutaneous fusion, insertion of drug delivery systems, and radiation delivery. In this situation, localization of reference points on the body elements must be determined by some form of imaging which can localize through overlying soft tissue and/or discriminate surrounding tissue and structures. There are currently two imaging techniques which are available to a surgeon in the operating room or a doctor in a procedure room which satisfy the needs of being low cost and portable. Both imaging techniques, ultrasonography and radiography, can produce two- or three-dimensional images which can be employed in the fashion described herein to register a three-dimensional form such as a skeletal element.

Figure 6:
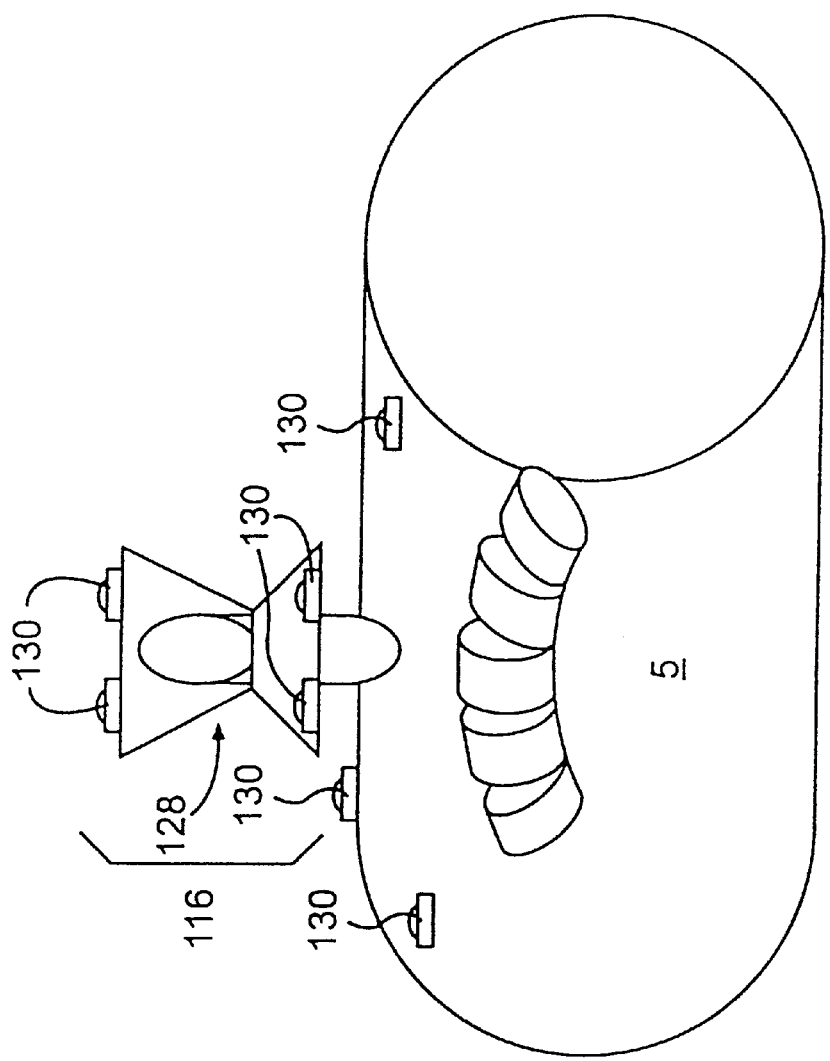
FIG. 6 is an illustration showing ultrasound registration according to the invention in which emitters are attached to the ultrasound for a virtual reference and, optionally, the patient's body for an actual reference.

As described in U.S. patent application Ser. Nos. 07/858, 980 and 08/053,076, the entire disclosures of which are incorporated herein by reference, the coupling of a three-dimensional digitizer to a probe of an ultrasound device affords benefits in that a contour can be obtained which can be related directly to a reference system that defines three-dimensional coordinates in the procedural work space, i.e., the surgical space. In the context of the present invention, a patient is imaged prior to a procedure to generate a pre-procedural image data set which is stored in memory 106. In the procedure room, the patient's body is immobilized to stabilize the spatial relationship between the body elements 10, 20, 30. A procedural reference system, surgical space, for the body is established by attaching a reference frame 116 to one of the body elements or by otherwise attaching emitters to the patient or body elements as noted above, or by attaching emitters to a device capable of tracking one of the body elements thereby forming a known relationship with the body element. For example, this could be performed by using the percutaneous placement of a reference frame similar to the one described above, radiopaque markers screwed into the elements or by placing emitters 130 directly on the skins, as illustrated in FIG. 6, based on the assumption that the skin does not move appreciably during the procedure or in respect to the body elements.

An ultrasound probe 128 equipped with at least three emitters 130 is then placed over the body element of interest. The contour (which can be either two- or three-dimensional) of the body element is then obtained using the ultrasound probe 128. This contour can be expressed directly or indirectly in the procedural coordinates defined by the reference system (surgical space). Emitters 130 communicate with sensors 112 of reference array 110 to indicate the position of the ultrasound probe 128. An ultrasound scanner 166 which energizes probe 128 to determine the contour of the body element of interest being scanned. This contour information is provided to processor 104 for storage in intra-procedural geometry data memory 121.

The intra-procedural contour stored in memory 121 is then compared by a contour matching algorithm to a corresponding contour extracted from the pre-operative image data set stored in memory 106. Alternatively, a pre-procedural contour data set may be stored in memory 134 based on a pre-procedural ultrasound scan which is input into memory 134 via scanner interface 102 prior to the procedure. This comparison process continues until a match is found for each one of the elements. Through this contour matching process, a registration is obtained between the images of each body element and the corresponding position of each element in the procedural space, thereby allowing the formation of the displaced image data set 122 used for localization and display. Note that the contours used in the matching process only have to be sufficiently identical to accomplish a precise match—the contours do not have to be the same extent of the body element.

In certain instances, the ultrasound registration noted above may not be applicable. For example, ultrasound does not penetrate bone, and the presence of overlying bone would preclude the registration of an underlying skeletal element. Further, the resolution of ultrasound declines as the depth of the tissue being imaged increases and may not be useful when the skeletal element is so deep as to preclude obtaining an accurate ultrasonically generated contour. In these circumstances, a radiological method is indicated, which utilizes the greater penetrating power of x-rays.

Figure 7:
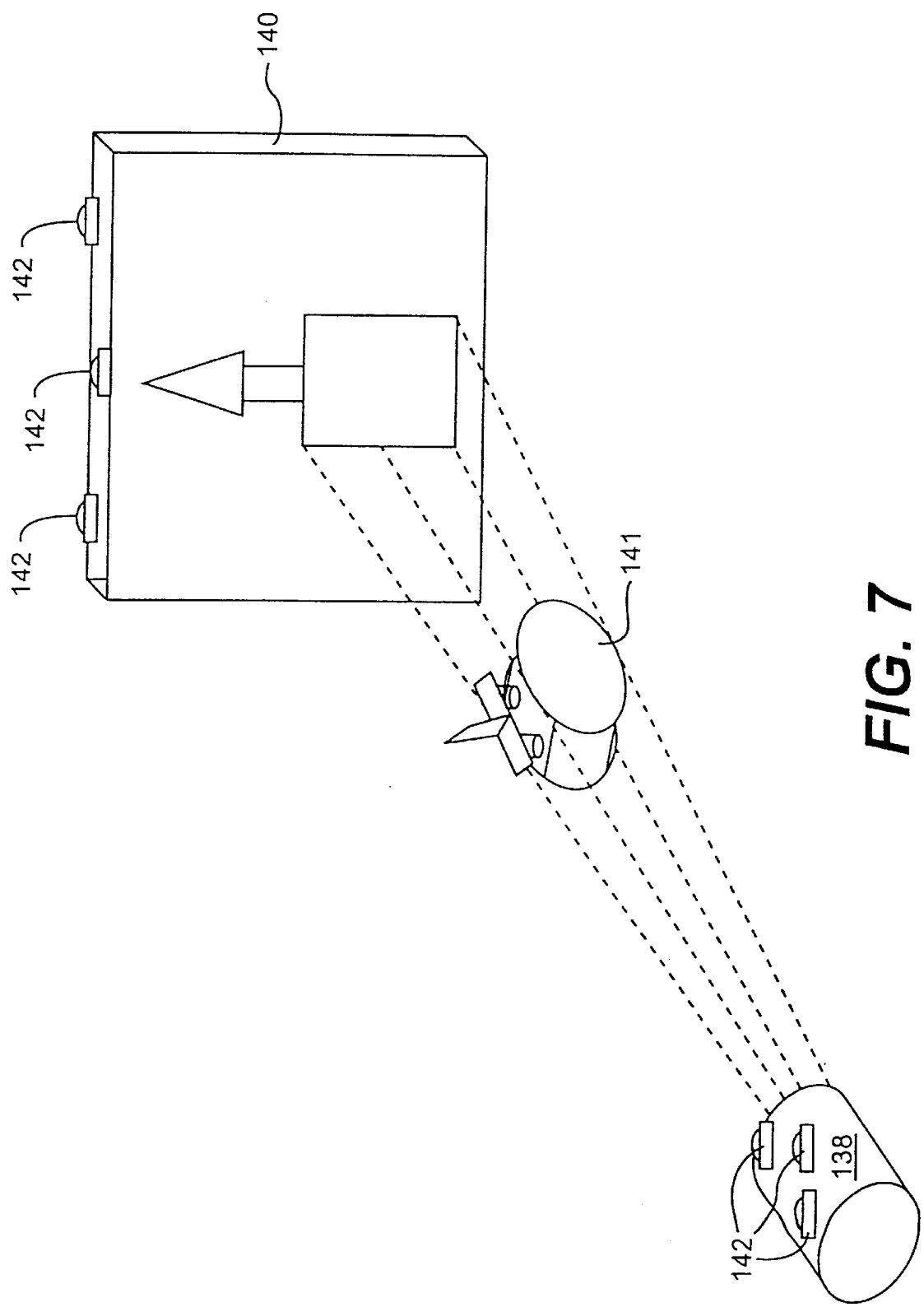
FIG. 7 is an illustration of a fluoroscopic localizer according to the invention for providing projections of an image of the body elements.

Pre-operative imaging occurs as usual and the skeletal elements may be discriminated from the soft tissue in the image data set as above. In particular, a CT scan of the skeletal elements 10, 20, 30 could be taken prior to the procedure. Processor 104 may then discriminate the skeletal elements and store the pre-procedural image data set in memory 106. Next, the patient is immobilized for the procedure. A radiograph of the skeletal anatomy of interest is taken by a radiographic device equipped with emitters detectible by the digitizer. For example, a fluoroscopic localizer 136 is illustrated in FIG. 7. Localizer 136 includes a device which emits x-rays such as tube 138 and a screen 140 which is sensitive to x-rays, producing an image when x-rays pass through it. This screen is referred to as a fluoroscopic plate. Emitters 142 may be positioned on the tube 138, or on the fluoroscopic plate 140 or on both. For devices in which the tube 138 is rigidly attached to the plate 140, emitters need only be provided on either the tube or the plate. Alternatively, the reference array 110 may be attached to the tube or the plate, obviating the need for emitters on this element. By passing x-rays through the skeletal element 141 of interest, a two-dimensional image based on bone density is produced and recorded by the plate. The image produced by the fluoroscopic localizer 136 is determined by the angle of the tube 138 with respect to the plate 140 and the position of the skeletal elements therebetween and can be defined with respect to procedure coordinates (surgical space). Fluoroscopic localizer 136 includes a processor which digitizes the image on the plate 140 and provides the digitized image to processor 104 for possible processing and subsequent storage in intra-procedural geometry data memory 121. Processor 104 may simulate the generation of this two-dimensional x-ray image by creating a series of two-dimensional projection of the three-dimensional skeletal elements that have been discriminated in the image data set stored in memory 106. Each two dimensional projection would represent the passage of an X-ray beam through the body at a specific angle and distance. In order to form the displaced data set and thus achieve registration, an iterative process is used which selects that a two-dimensional projection through the displaced data-set that most closely matches the actual radiographic image(s) stored in memory 121. The described process can utilize more than one radiographic image. Since the processor 104 is also aware of the position of the fluoroscopic localizers because of the emitters 142 thereon, which are in communication with localizer 108, the exact position of the skeletal elements during the procedure is determined.

As noted above, the procedural reference system or surgical space for the body can be established by attaching emitters to a device capable of detecting and tracking, i.e. identifying, one of the body elements thereby forming a known relationship with the body element. For example, the emitters 130 on the ultrasound probe 128 together and without the three emitters on the patient's body form a type of reference frame 116 as depicted in FIG. 6 which can be virtually attached to body element 10 by continuously or periodically updating the ultrasound contour of body element 10 stored in intra-procedural geometry data memory 121 which the processor 104 then uses to match to the contour of body element 10 stored in pre-procedural memory 106 thereby continuously or periodically updating the displaced image data set in memory 122 so that registration with the procedural position of the body elements is maintained. It is contemplated that a virtual reference frame can be accomplished using any number of devices that are capable of detecting and tracking a body element such as radiographic devices (fluoroscope), endoscopes, or contour scanners.

The above solutions achieve registration by the formation of a displaced image data set stored in memory 122 which matches the displacement of the skeletal elements at the time of the procedure. An alternative technique to achieve registration is to ensure that the positions of the skeletal elements during the procedure are identical to that found at the time of imaging. This can be achieved by using a frame that adjusts and immobilizes the patient's position. In this technique, at least three markers are placed on the skin prior to imaging. These markers have to be detectible by the imaging technique employed and are called fiducials. A multiplicity of fiducials is desirable for improving accuracy.

During the procedure, the patient's body is placed on a frame that allows precise positioning. Such frames are commonly used for spinal surgery and could be modified to allow their use during imaging and could be used for repositioning the patient during the procedure. These frames could be equipped with drive mechanisms that allow the body to be moved slowly through a variety of positions. The fiducials placed at the time of imaging are replaced by emitters. By activating the drive mechanism on the frame, the exact position of the emitters can be determined during the procedure and compared to the position of the fiducials on the pre-procedural image data set stored in memory 106. Once the emitters assume a geometry identical to the geometry of the fiducials of the image data set, it is considered that the skeletal elements will have resumed a geometric relationship identical to the position during the pre-procedural scan, and the procedure can be performed using the unaltered image data set stored in memory 106.

In general, instrumentation employed during procedures on the skeleton is somewhat different than that used for cranial applications. Rather than being concerned with the current location, surgery on the skeleton usually consists of placing hardware through bones, taking a biopsy through the bone, or removing fragments. Therefore, the instrumentation has to be specialized for this application.

Figure 8:
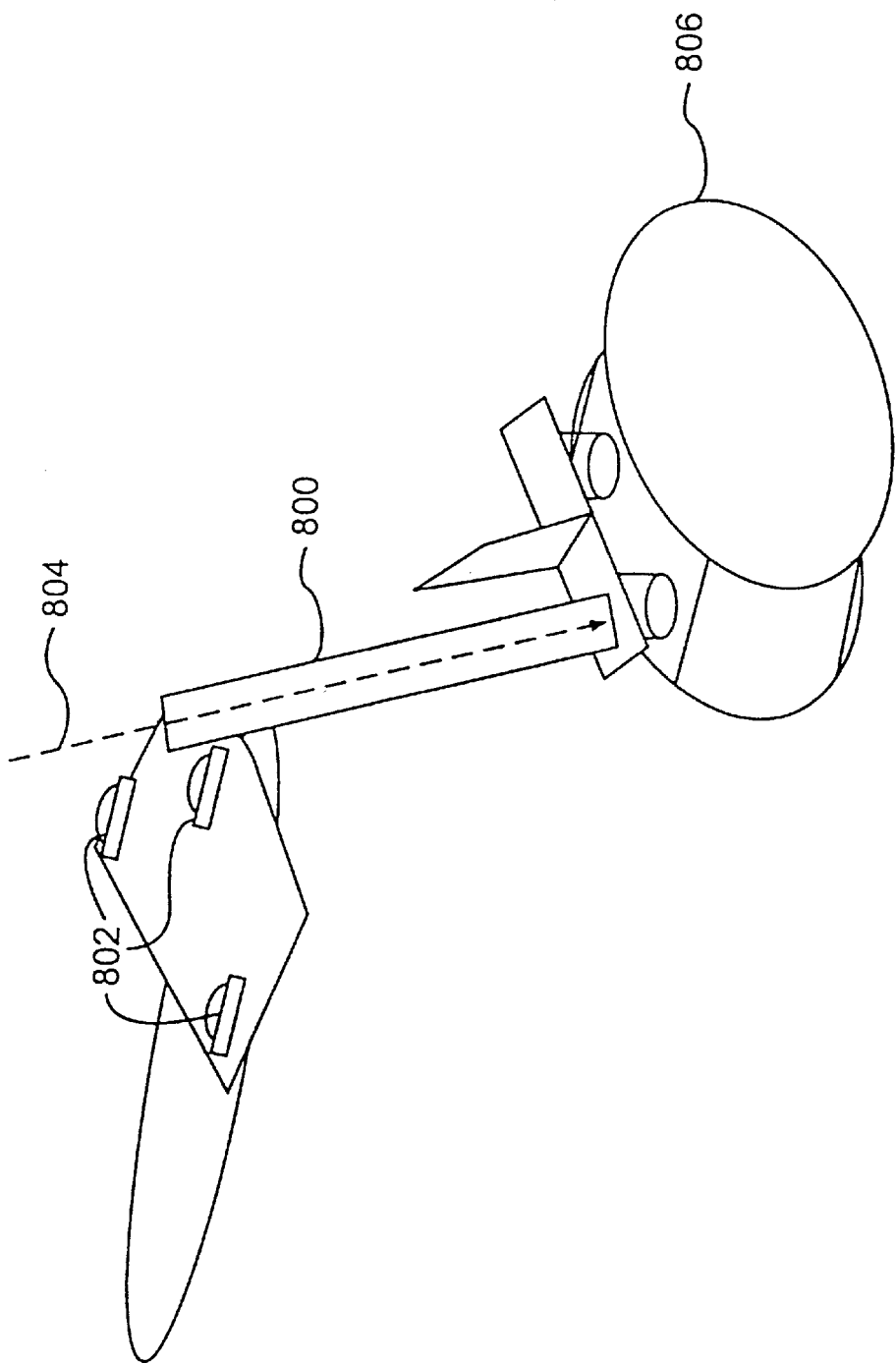
FIG. 8 is an illustration of a drill guide instrument of the invention wherein the position of a drill guide relative to the body elements may be displayed.

One instrument that is used commonly is a drill. By placing emitters on a surgical drill, and by having a fixed relationship between the drill body and its tip (usually a drill bit), the direction and position of the drill bit can be determined. At least three emitters would be needed on the drill, as most drills have a complex three-dimensional shape. Alternatively, emitters could be placed on a drill guide tube 800 having emitters 802, and the direction 804 of the screw being placed or hole being made could be determined by the digitizer and indicated on the image data set (see FIG. 8). The skeletal element 806 would also have emitters thereon to indicate its position.

Besides modification of existing instrumentation, new instrumentation is required to provide a reference system for surgery as discussed above. These reference frames, each equipped with at least 3 emitters, require fixation to the bone which prevents movement or rotation.

Figure 9:
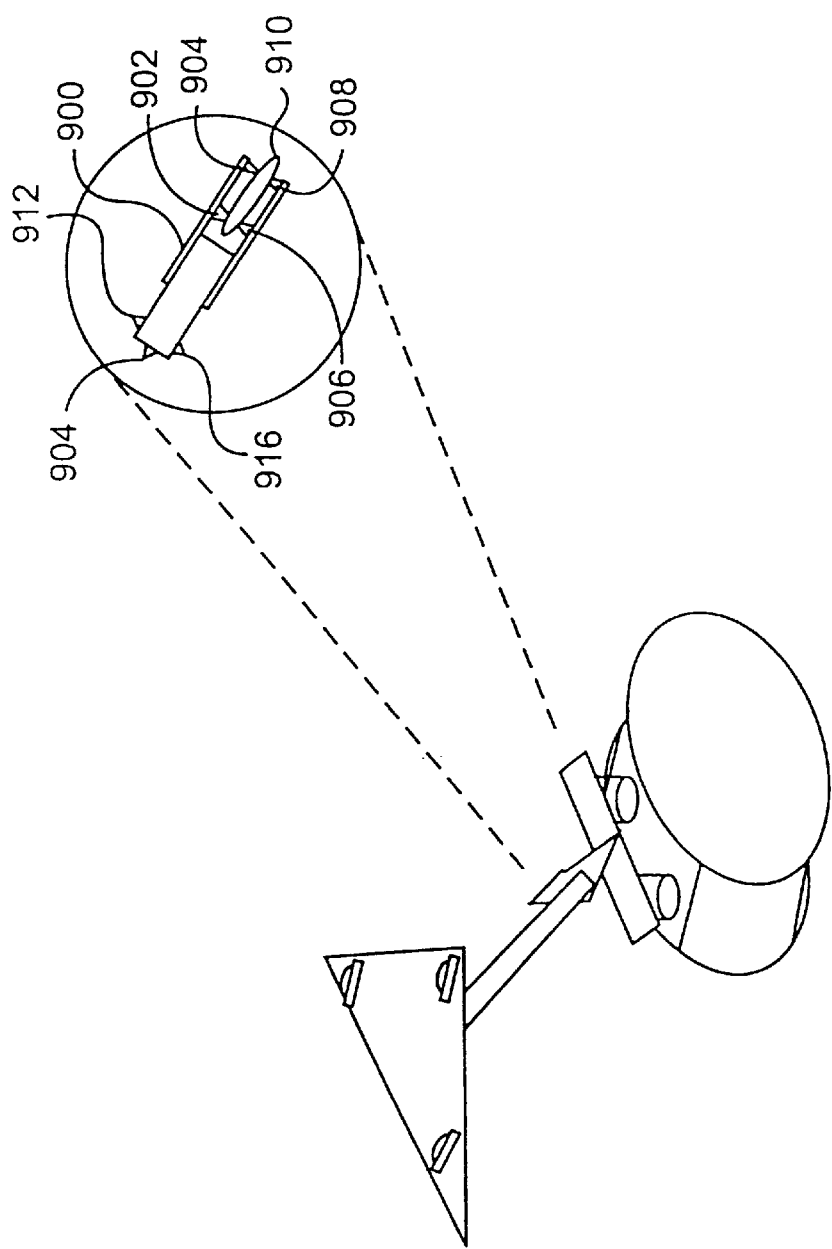
FIGS. 9 and 10 illustrate a clamped reference frame and a wired reference frame, respectively.

For open surgery, a clamp like arrangement, as depicted in FIG. 9, can be used. A clamp 900 is equipped with at least two points 902, 904, 906, 908 which provide fixation to a projection 910 of a skeletal element. By using at least two point fixation the clamp 900, which functions as a reference frame, will not rotate with respect to the skeletal element. The clamp includes emitters 912, 914, 916 which communicate with the array to indicate the position of the skeletal element as it is moved during the procedure.

Figure 10:
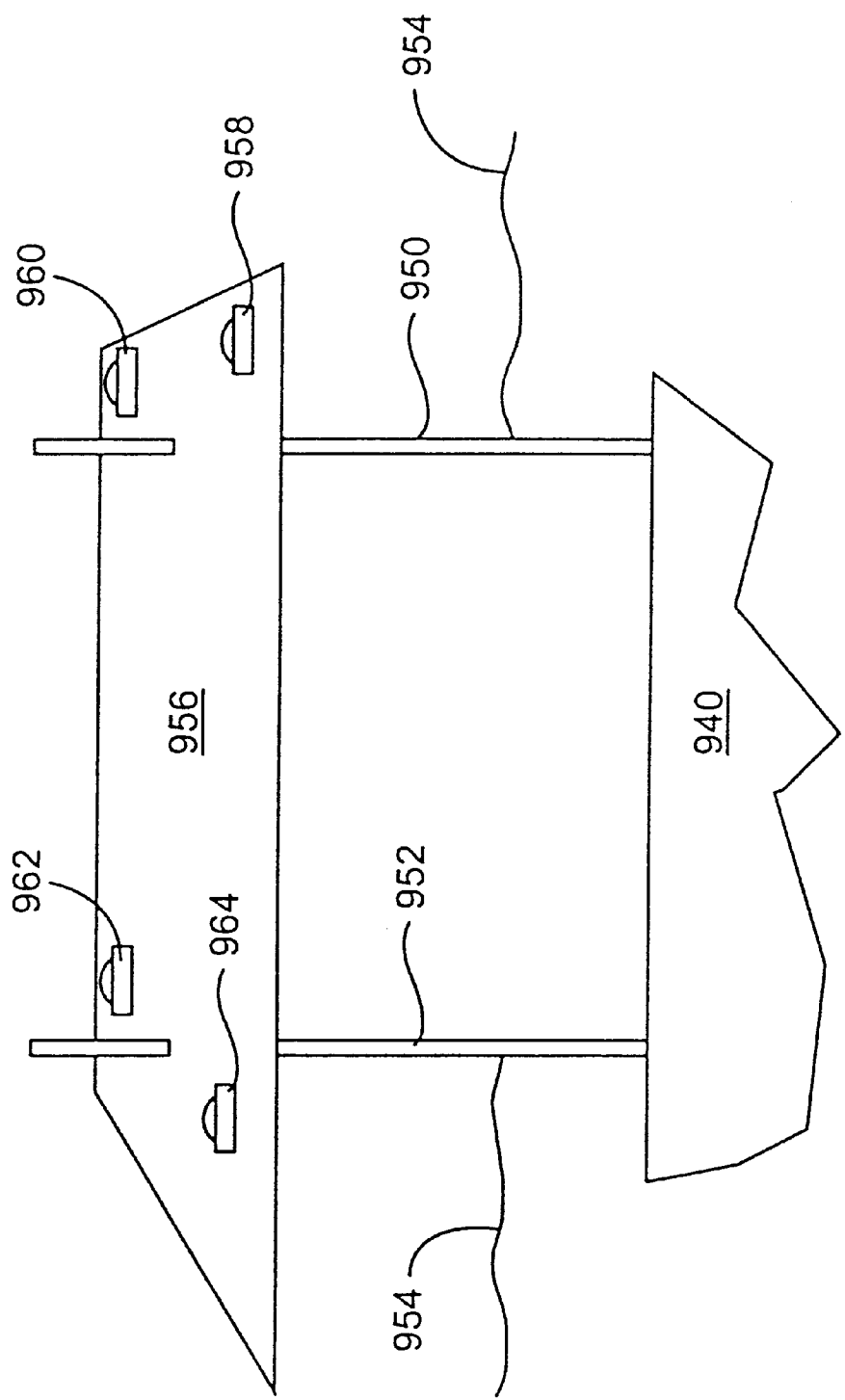

Many procedures deal with bone fragments 940 which are not exposed during surgery, but simply fixated with either wires or screws 950, 952 introduced through the skin 954. FIG. 10 depicts a reference platform 956 attached to such wires or screws 950, 952 projecting through the skin 954. The platform 956 includes a plurality of emitters 958, 960, 962, 964 which communicate with the array to indicate the position of the bone fragment 940 as it is moved during the procedure.

The reference frame can be slipped over or attached to the projecting screws or wires to establish a reference system. Alternatively, the frame can be attached to only one wire, as long as the method of attachment of the frame to the screw or wire prevents rotation, and that the wire or screw cannot rotate within the attached skeletal element.

Reference and Localization Frames

Figure 11:
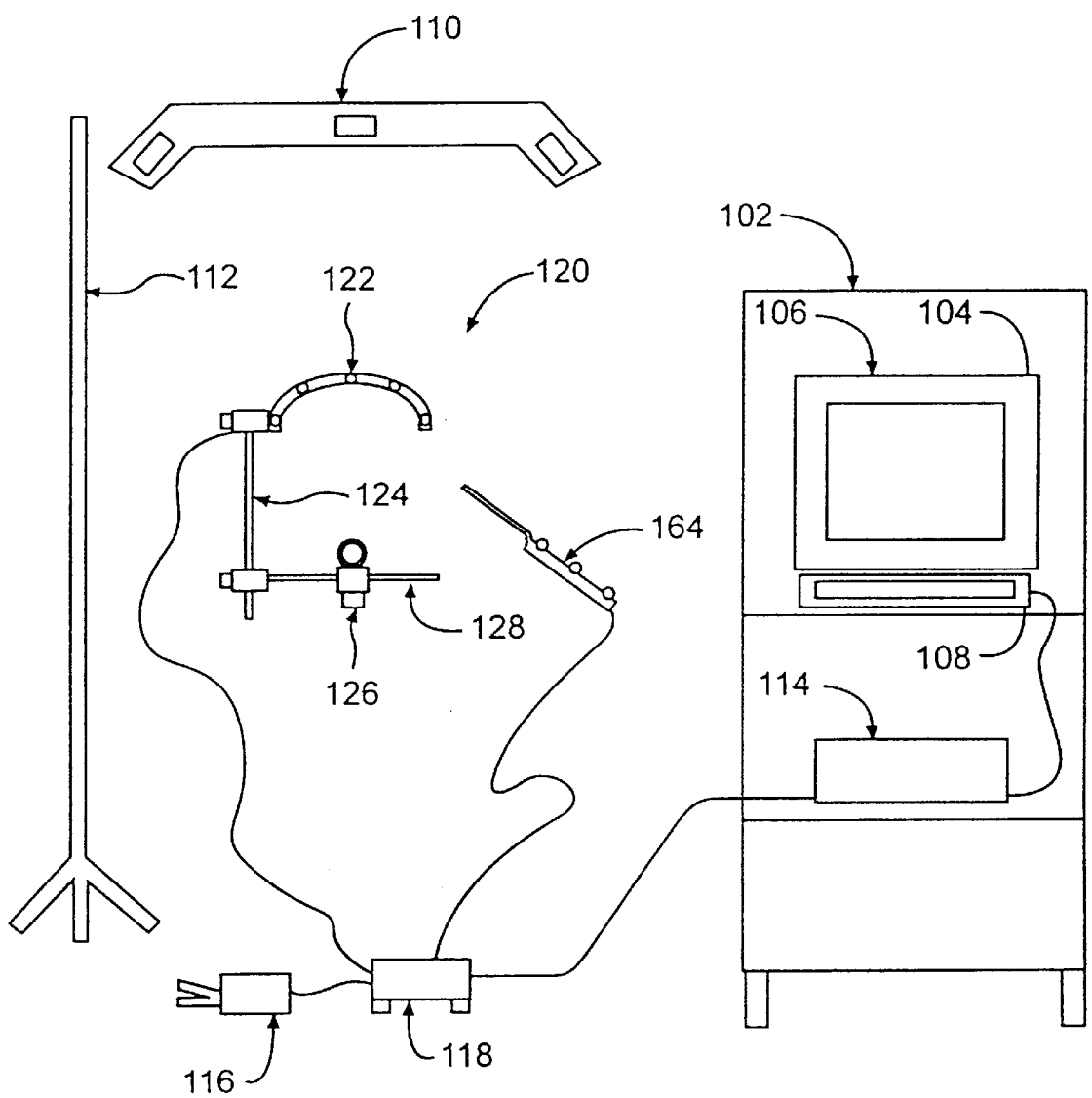
FIG. 11 is a schematic diagram of one preferred embodiment of a cranial surgical navigation system according to the invention.

FIG. 11 is a schematic diagram of one preferred embodiment of a cranial surgical navigation system according to the invention. Portable system cabinet 102 includes a surgical work station 104 which is supported for viewing by the surgeon or technician using the system. Work station 104 includes a screen 106 for illustrating the various scans and is connected to a personal computer 108 for controlling the monitor 106. The system also includes an optical digitizer including a camera array 110, a camera mounting stand 112 for supporting the array remote from and in line of sight with the patient, a digitizer control unit 114 on the portable system cabinet 102 and connected to the computer 108, a foot switch 116 for controlling operation of the system and a breakout box 118 for interconnecting the foot switch 116 and the digitizer control unit 114.

Also connected via the break out box 118 is a reference frame assembly 120 including a reference frame 122 with cable connected to the break out box 118, a vertical support assembly 124, a head clamp attachment 126 and a horizontal support assembly 128. Optical probe 164 (which is a localization frame) is also connected via cable to the digitizer control unit 114 via the break out box 118.

In operation, a patient's head (or other "rigid" body element) is affixed to the head clamp attachment 126. To determine the position of optical probe 164 with respect to the head within the head clamp attachment 126, a surgeon would step on pedal 116 to energize the emitters of reference frame 122. The emitters would generate a light signal which would be picked up by camera array 110 and triangulated to determine the position of the head. The emitters of the optical probe 130 would also be energized to emit light signals which are picked up by the camera array to determine the position of the optical probe 164. Based on the relative position of the head and the probe 164, control box 114 would illustrate a preoperative scan on the screen of monitor 106 which would indicate the position of the probe relative to and/or within the head.

Figure 11A:
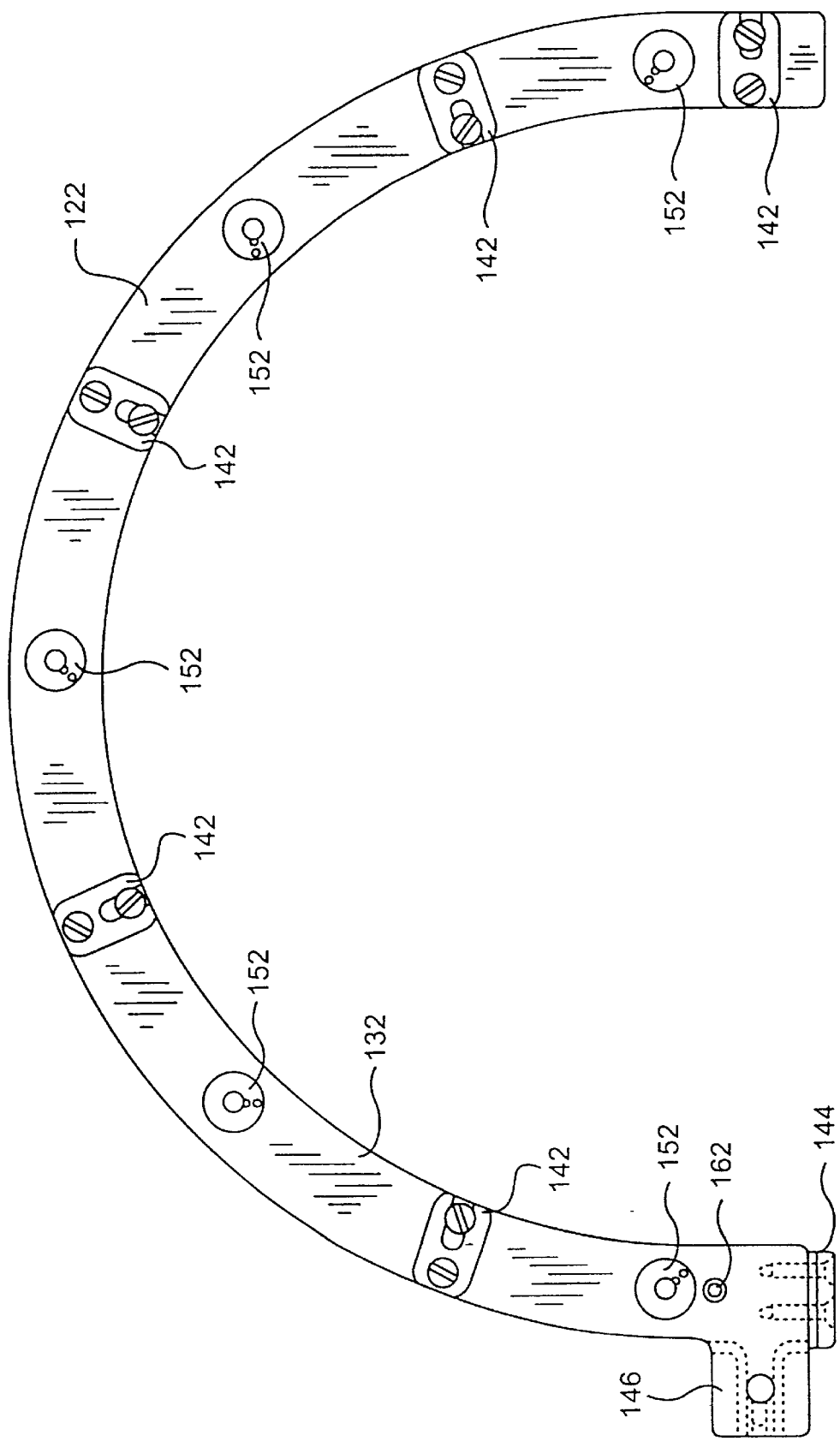
FIG. 11A is a top plan view of one preferred embodiment of a cranial reference arc frame according to the invention.

FIG. 11A is a top plan view of one preferred embodiment of a cranial reference arc frame 122 according to the invention. Reference frame 122 is for use with a surgical navigation system such as illustrated in FIG. 11 having a sensor array such as camera array 110 which is in communication with the reference frame 122 to identify its position. The reference frame 122 includes a base member 132 having an upper base 134 and a base plate 136 which each have a semi-circular configuration and are joined together by screws 138 to form a cavity 140 therebetween. The base and plate may be made of anodized aluminum or other autoclavable material. The top of the upper base may be provided with one or more spring clamps 142 for engaging a Leyla retractor arm. As shown in FIG. 11A, the upper base is provided with five spring clamps 142.

Either or both ends of the reference frame 122 may be provided with a bayonet fitting 144 for engaging a clamp which would also engage a Leyla retractor. One or both ends of the reference frame 122 is also formed into a radial projection 146 for supporting a screw 148 and crank handle 150 used to lock the reference frame to a head clamp such as head clamp 126 shown in FIG. 11 or a Mayfield clamp. This allows the reference frame 122 to be placed in a fixed position relative to the head so that any movement of the head would also include corresponding movement of the reference frame 122.

Radial projection 146, screw 148 and handle 150 constitute a coupling on the base member 132 for engaging a structure attached to a body part (the head) thereby providing a fixed reference relative to the head in order to maintain the base member 132 in fixed relation to the head.

Figures 11B, 11C:
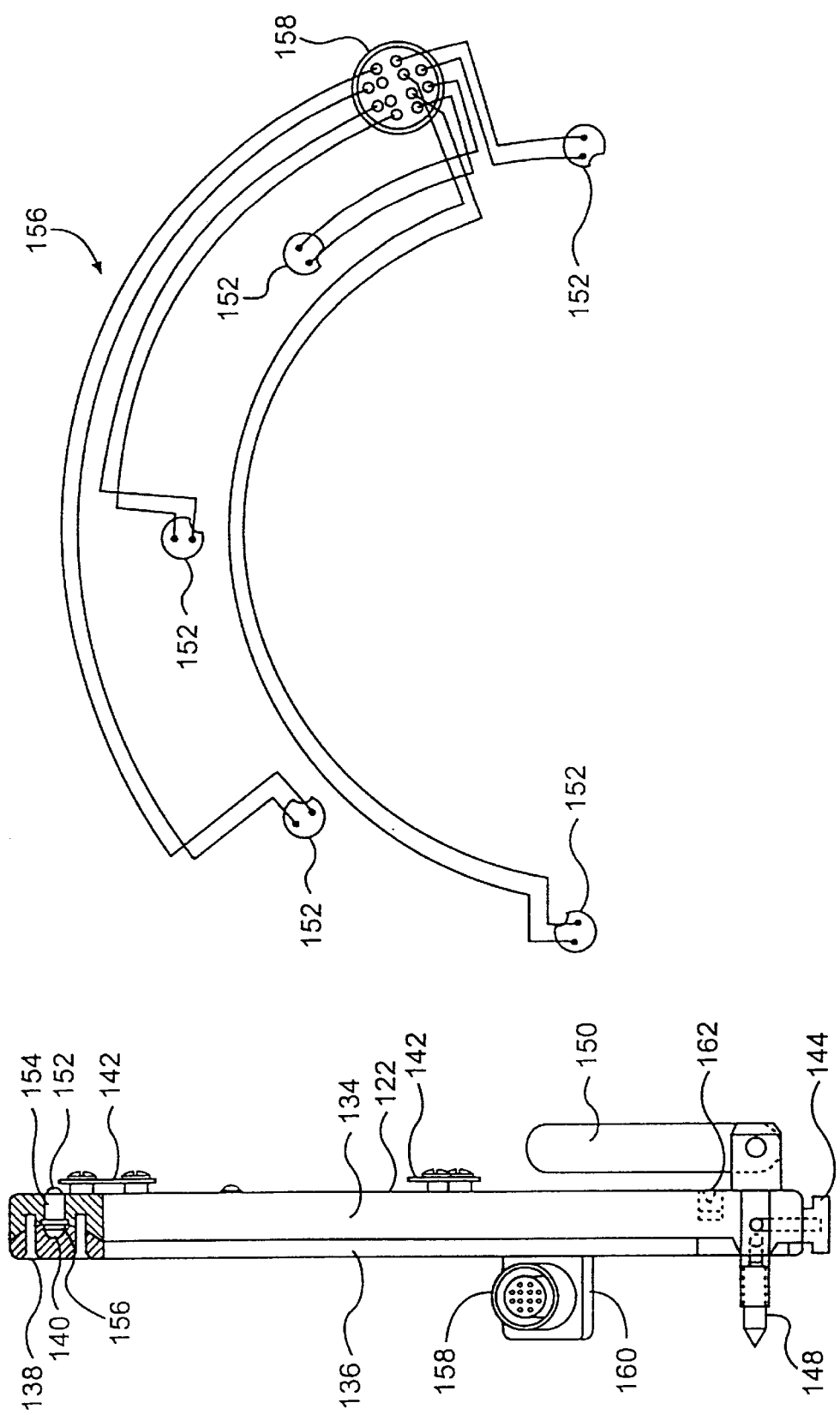
FIG. 11B is a side plan view, partially in cross section, of one preferred embodiment of a cranial reference arc frame according to the invention.
FIG. 11C is a wiring diagram of one preferred embodiment of a cranial reference arc frame according to the invention.

Equally spaced about the reference frame 122 are a plurality of LEDs 152 for communicating with the camera array 110. The LEDs 152 are mounted in holes 154 in the upper base 134, which holes 154 are in communication with the cavity 140. Wires 156 are connected to each of the terminals of the LEDs 152 are positioned within the cavity 140. The other ends of the wires are connected to a connector 158 for engaging a cable connected to the digitizer 114 of the surgical navigation system. The cable provides signals for activating the LEDs 152. Connector 158 is mounted on a support projection 160 which projects from the base plate 136. This support projection 160 has a channel therein for permitting the wires to be connected to the connector 128. FIG. 11A is a wiring digram of one preferred embodiment of the reference frame 122 according to the invention. As is illustrated in FIG. 11C, each LED terminal is connected to a separate pin of the connector 158. Although the invention is illustrated as having a connector for engaging a cable, it is contemplated that the reference frame 122 may be battery operated so-that no cable is necessary.

The reference frame 122 is essentially a semi-circular arc so that it fits around the head of the patient to allow communication of multiple LEDs 152 on the reference frame 122 with the camera array 110. The multiple LEDs 152 on the reference frame 122 are positioned in a precisely known geometric arrangement so that the calibration of the camera array 110 can be checked continuously by comparing the LEDs geometric positions as calculated by the digitizer 114 with those precisely known geometric positions. Inconsistencies in this information indicates the need to recalibrate the system or to reposition the reference frame 122 so that it can more accurately communicate with the camera array 110. Frame 122 also includes a calibration divot 162. In particular, divot 162 is an exactly located depression within the upper base 134 and is used to calibrate or check the calibration during the medical or surgical procedure the position of the tip of the probe. The precise location of each of the LEDs 152 relative to the calibration divot 162 is known. Therefore, locating a tip of a localization frame probe in the calibration divot 162 allows the calibration or the calibration check of the probes in the following manner. The tip of the probe is located within the calibration divot 162 and the LEDs on the probe are energized to provide light signals to the camera array 110. The LEDs on the reference frame 122 are also energized to communicate with the camera array 110. Using the known position of the divot 162 with respect to the position of each of the LEDs 152 as calculated by the digitizer 114, the location of the calibration divot 162 is compared to the location of the tip of the probe as calculated by the digitizer using the LEDs on the probe in order to confirm that there is no distortion in the probe tip relative to the divot 162. Distortion in the probe tip indicates the need to recalibrate the probe so that it can more accurately communicate with the camera array 110 or to retire the probe.

Figure 12A:
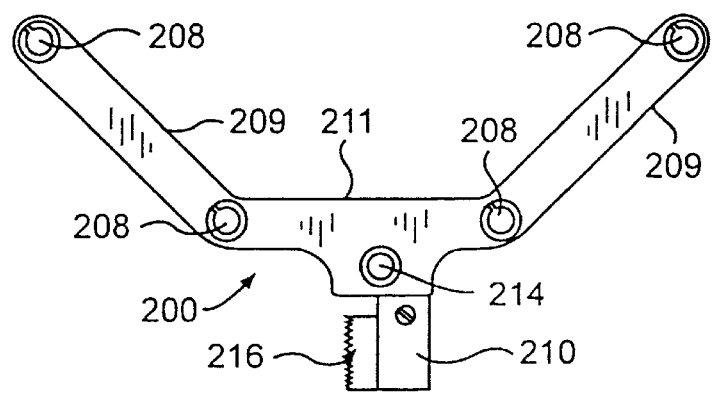
FIG. 12A is a top plan view of one preferred embodiment of a spinal reference arc frame according to the invention.
Figure 12B:
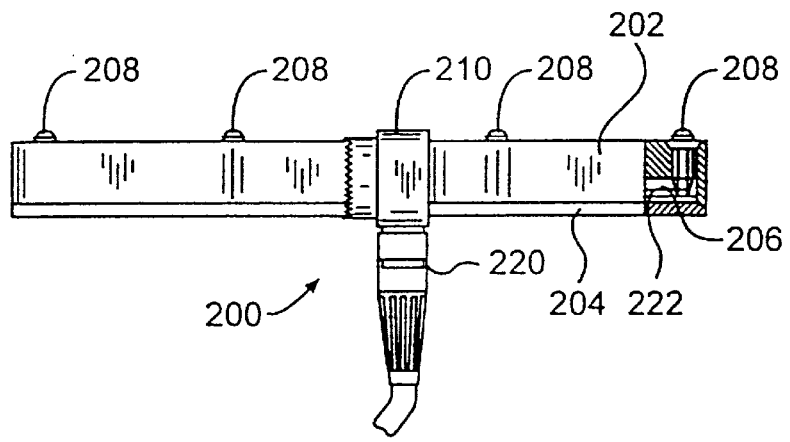
FIG. 12B is a front plan view, partially in cross section, of one preferred embodiment of a spinal reference arc frame according to the invention.
Figure 12C:
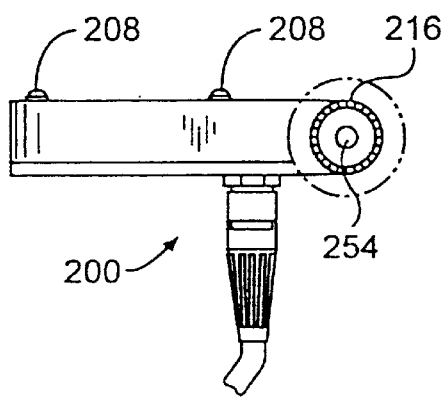
FIG. 12C is a side plan view of one preferred embodiment of a spinal reference arc frame according to the invention.
Figure 12D:
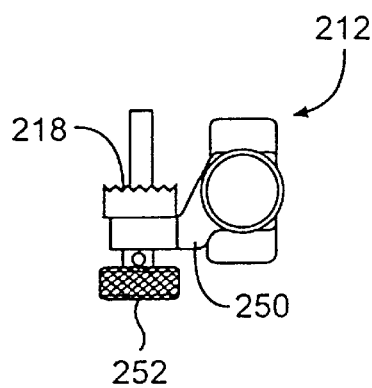
FIG. 12D is a top plan view of one preferred embodiment of a thoraco-lumbar mount according to the invention.
Figure 12E:
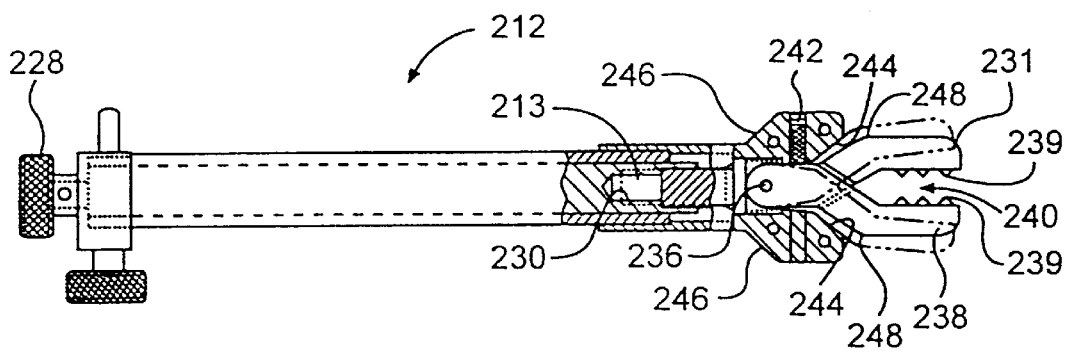
FIG. 12E is a front plan view, partially in cross section, of one preferred embodiment of a thoraco-lumbar mount according to the invention.
Figure 12F:
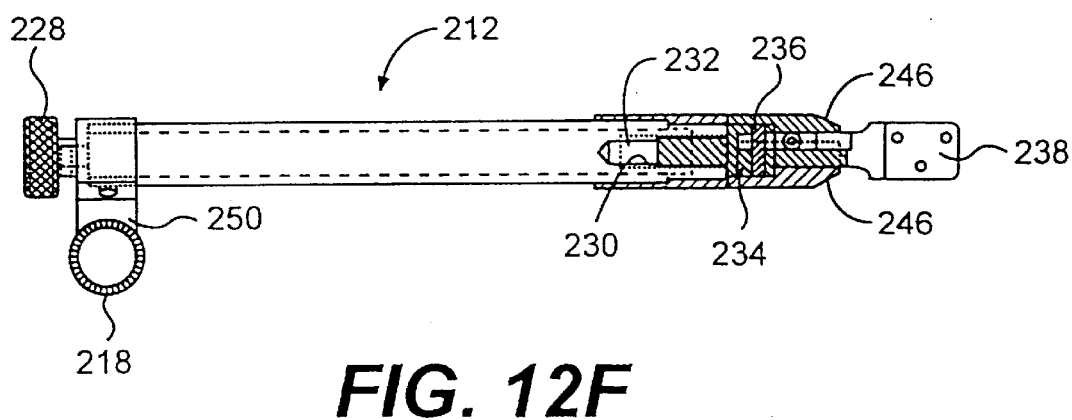
FIG. 12F is a side plan view of one preferred embodiment of a thoraco-lumbar mount according to the invention.

FIGS. 12A, 12B, and 12C illustrate another preferred embodiment of the reference frame in the form of a spine reference arc frame 200. As with reference frame 122, spine reference arc frame 200 has an upper base 202 which engages a base plate 204 to form a cavity 206 therebetween. As shown in FIG. 12A, the spine reference arc frame 200 has a generally U-shape configuration with LEDs 208 located at the ends of the legs 209 of the U-shaped member and at the intersection of the legs and base 211 of the U-shaped member. Projecting laterally from the base 211 is a coupling 210 for engaging a thoraco-lumbar mount 212 as illustrated in FIGS. 12D, 12E, and 12F. Also positioned on the base 211 is a calibration divot 214 which is a depression having the same purpose as the calibration divot 162 of the reference frame 122. Coupling 210 has twenty-four evenly spaced teeth 216 arranged in a circular pattern for engaging the twenty-four equally spaced teeth 218 of the thoraco-lumbar mount. This allows the spine reference arc frame 200 to be positioned to form various angles relative to the mount 212. It is contemplated that any other variable position connector may be used to join the spine reference arc frame 200 and the mount 212. Base plate 204 has an opening therein for engaging a connector 220 for receiving a cable to the digitizer control unit 114. The LEDs 208 are connected to the connector 220 by wires 222 as illustrated in wiring diagram FIG. 12G.

Referring to FIGS. 12D, 12E, and 12F, thoraco-lumbar mount 212 comprises a clamp shaft 224 having an axial bore therein within which is positioned an actuating shaft 226 which is connected to an actuating knob 228 extending beyond the end of clamp shaft 224. The end of the actuating shaft 226 opposite the actuating knob 228 has an internal threaded bore 230 which engages external threads of an actuation screw 232. A U-shaped head 234 of screw 232 supports a pivot pin 236 between its legs. The pivot pin passes through the jaws 238 so that the jaws 238 rotate about the pivot pin 236 and move relative to each other defining a receiving area 240 within which a spinal bone or other body part may be clamped. The jaws 238 have teeth 239 for engaging a spinal bone or other body part and are spring loaded and held in their open position by spring plungers 242. As the actuating knob 228 is turned to engage the threads of actuation screw 232, the screw 232 is drawn into the bore 230 also drawing the jaws into a housing 246. This results in the camming surfaces 244 of housing 246 engaging the follower surfaces 248 of the jaws 238 closing the jaws and closing the receiving area 240 as the jaws are pulled into the housing.

The other end of clamp shaft 224 has a perpendicular projection 250 for supporting the teeth 218 which engage the teeth 216 of the coupling 210 of the spine reference arc frame 200. A spine reference arc clamp screw 252 passes through the array of teeth 218 and engages a threaded opening 254 in the coupling 210 of frame 200. Screw 252 engages opening 254 and locks teeth 216 and teeth 218 together to fix the angle between the spine reference arc frame 200 and the thoraco-lumbar mount 212. As a result, when the mount 212 is connected to a bone by placing the bone in the receiving area 240 and turning the actuating knob 228 to close the jaws 238 and the receiving area, the frame 200 is in a fixed position relative to the bone which is engaged by the jaws. Any movement of the bone results in movement of the frame 200 which can be detected by the camera array 110.

Figure 13A:
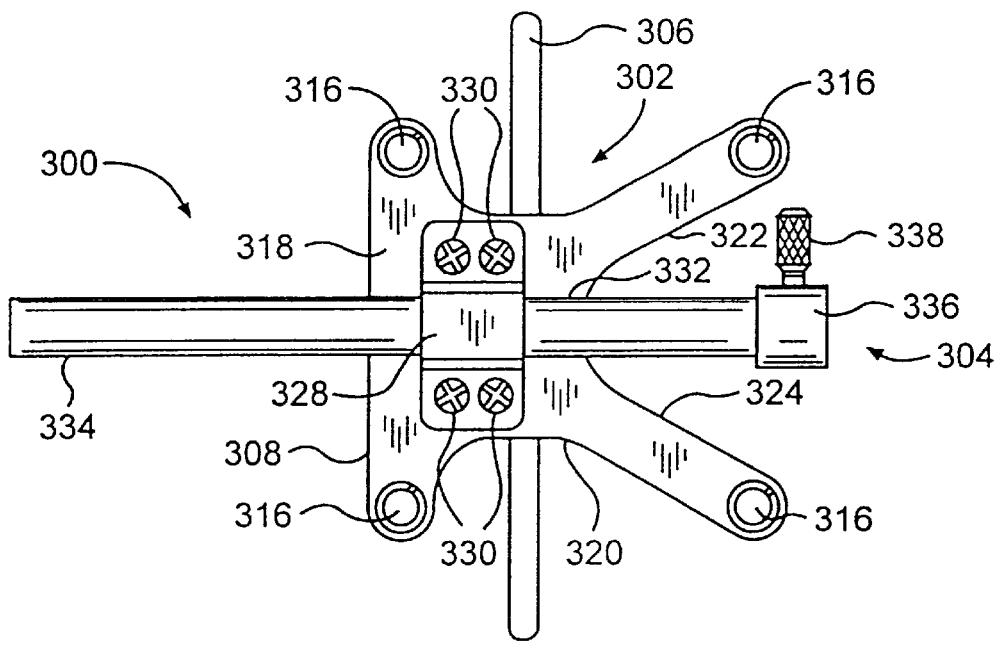
FIG. 13A is a top plan view of one preferred embodiment of a biopsy guide localization frame according to the invention.
Figure 13B:
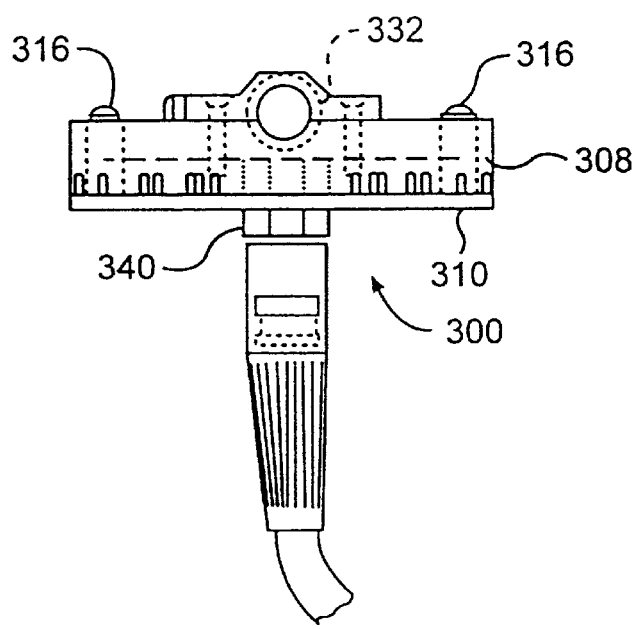
FIG. 13B is a side plan view, partially in cross section, of one preferred embodiment of a biopsy guide localization frame according to the invention.
Figure 13C:
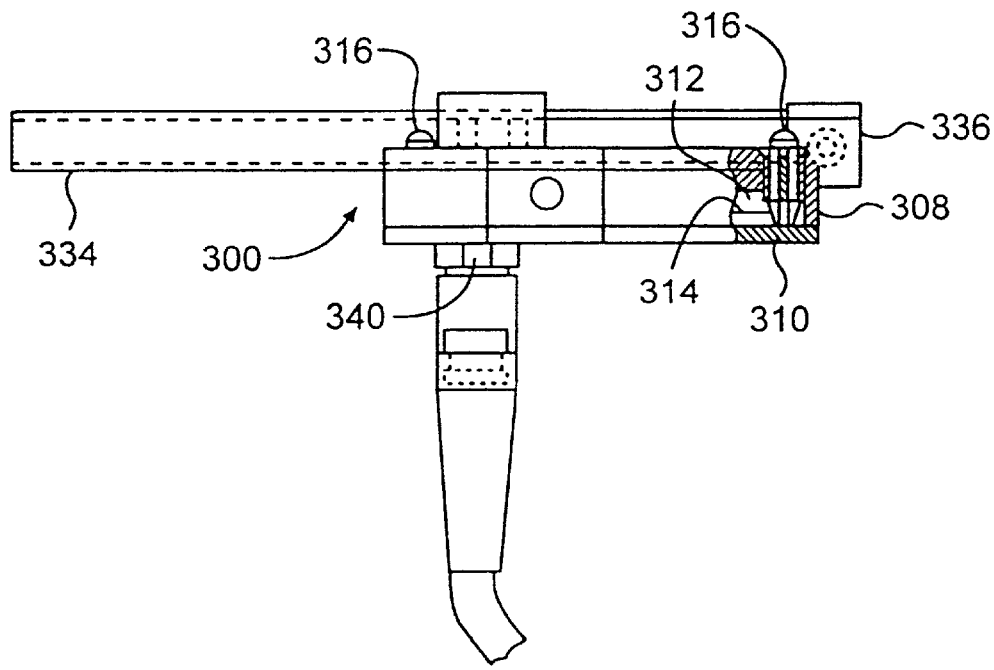
FIG. 13C is a front plan view of one preferred embodiment of a biopsy guide localization frame according to the invention.

Referring to FIGS. 13A, 13B and 13C, one preferred embodiment of a localization biopsy guide frame 300 is illustrated. In general, the frame 300 includes a localization frame 302 which supports a biopsy guide 304 and which also supports a support pin 306. The localization frame 302 is comprised of an upper base 308 and a base plate 310 which join to form a cavity 312 within which the wires 314 connecting to the LEDs 316 are located. As shown in the FIG. 13A, the localization frame has an elongated portion 318 and a generally V-shaped portion 320 having legs 322 and 324. An LED 316 is located at the end of each of the legs 322 and an LED 316 is also located at the ends of the elongated portion 318. As a result the four LEDs 316 form a rectangular array. However, the underlying localization frame 302 does not have a rectangular configuration which allows it to be adapted for other uses, such as a drill guide assembly as illustrated and described below with regard to FIGS. 13D and 13E. In general, the V-shaped portion 320 extends laterally from the elongated portion 318 in order to accomplish the rectangular configuration of the LEDs 316. Note that a rectangular configuration for the LEDs 316 is not required and that in fact, a trapezoidal configuration for the LEDs 316 may be preferred in order to uniquely distinguish the orientation of the localization frame 302. Support pin 306 passes through the upper base 308 and is essentially parallel to a linear axis defined by the elongated portion 318. The purpose of support pin 306 is to allow clamps to engage it so that the localization biopsy guide frame 300 can be placed in a particular position relative to a body part in order to guide a biopsy needle.

In order to guide a biopsy needle, the localization frame 302 is fitted with a biopsy guide 304 which is mounted to the top of the upper base 308 and held in place by a clamp 328 which engages the upper base 308 via four screws 330. The upper base 308 is also provided with a semicircular channel 332 which forms a seat for receiving the biopsy guide 326. The guide 304 comprises a hollow tube 334 having a collar 336 at one end thereof, which has a threaded radial opening for receiving set screw 338.

Figure 12G:
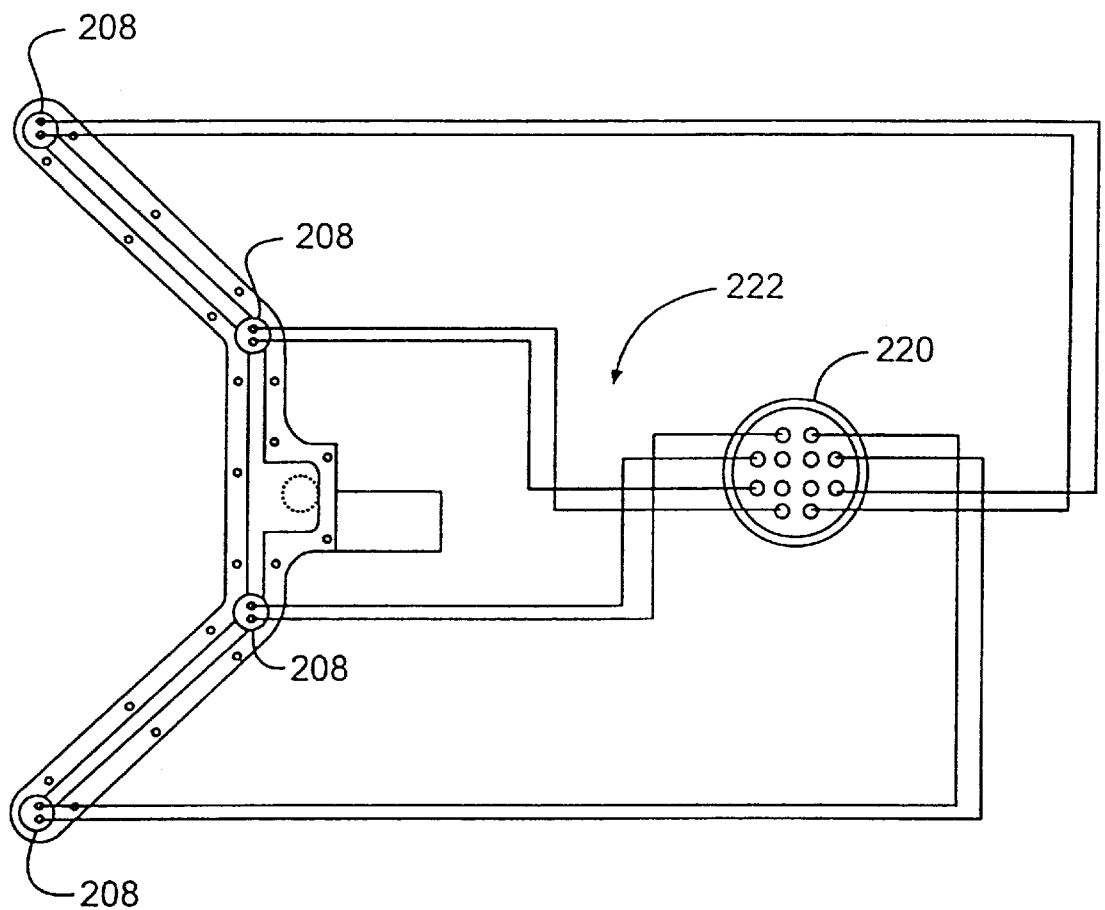
FIG. 12G is a wiring diagram of one preferred embodiment of a spinal reference arc frame according to the invention.

The base plate 310 is fitted with a connector 340 for engaging a cable which is connected to the digitizer 114 for providing signals for energizing the LEDs 316. FIG. 12G illustrates one preferred embodiment of a wiring diagram which interconnects the connector 340 and four LEDs.

The localization frame 302 is made of the same material as the reference frame 122, i.e., ULTEM 1000 black which is autoclavable. The biopsy guide 304 may be stainless steel or any other autoclavable metal or plastic material. As with the reference frame, the localization frame may be battery operated thereby avoiding the need for a cable or a connector for engaging the cable.

Figure 13D:
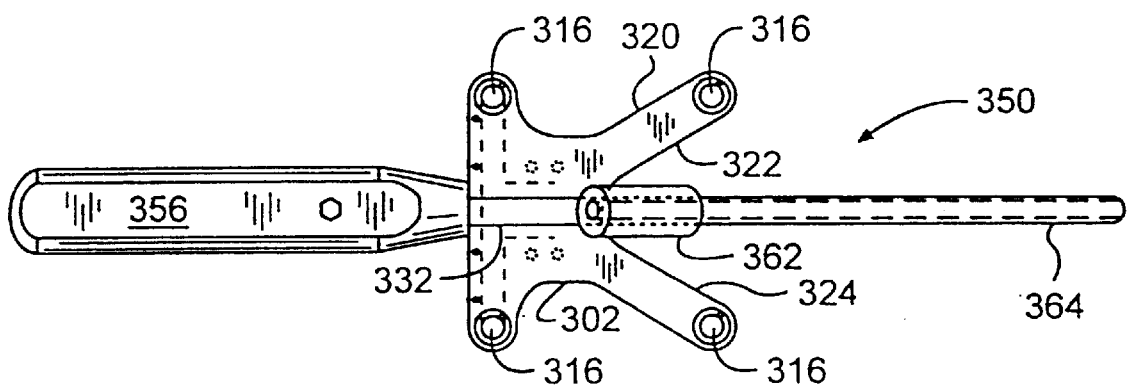
FIG. 13D is a top plan view of one preferred embodiment of a drill guide localization frame according to the invention.
Figure 13E:
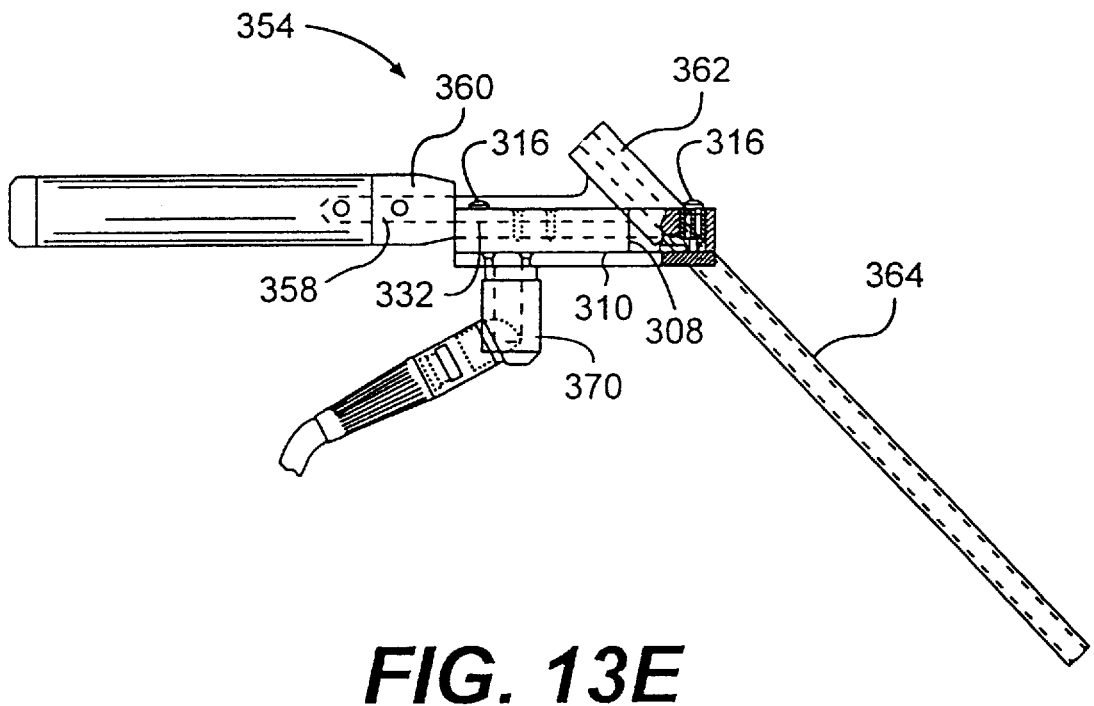
FIG. 13E is a side plan view, partially in cross section, of one preferred embodiment of a drill guide localization frame according to the invention.

FIGS. 13D and 13E illustrate another localization device in the form of a localization drill guide assembly 350. The assembly 350 includes a localization frame 302 which is the same as the frame used for the localization biopsy guide frame 300, except that it does not have a support pin 306. It does have a semicircular channel 332 in the upper base 308 which receives a handle and drill guide assembly 354 instead of the biopsy guide tube assembly 304. Assembly 354 includes a handle 356 which is used by the surgeon, doctor, technician or nurse conducting the procedure. Handle 356 has a bore 358 therein for receiving a shaft 360 which is seated within the semicircular channel 332. The shaft terminates into an integral collar 362 which supports a drill guide tube 364. The axis of the drill guide tube 364 is at an angle relative to the axis of the shaft 360 to assist in aligning the drill guide tube 364 relative to the point at which the drill bit will be entering the patient's body. In one preferred embodiment, handle and drill guide assembly 354 is a standard off-the-shelf instrument which is mounted to the channel 332 of the localization frame 302. The handle and drill guide assembly 354 may be a Sofamor Danek Part 870-705. Screws 366 (having heads insulated with high temperature RTV compound) attach the shaft 360 to the upper base 308 of the localization frame 302 and hold the shaft 360 in place within the channel 332. As noted above, the V-shaped portion 320 of the localization frame 302 forms an opening 368 between its legs 322 and 324 so that the drill guide tube 364 may be located therebetween and project downwardly from the plane generally defined by the localization frame 302. This allows the surgeon to sight in the position of the drill guide tube 364 by looking through the tube. Connector 370 is similar to connector 340, except that it provides an angular engagement with the cable which allows for more freedom of movement of the localization drill guide assembly 350. As with the localization frame noted above, the frame itself is made of ULTEM 1000 which is autoclavable. The handle may be wood, plastic, or any other autoclavable material and the shaft, collar and drill guide may be metal, plastic or other autoclavable material, such as stainless steel. FIG. 13K illustrates a preferred embodiment of the wiring diagram for the localization drill guide assembly 350.

Figure 13F:
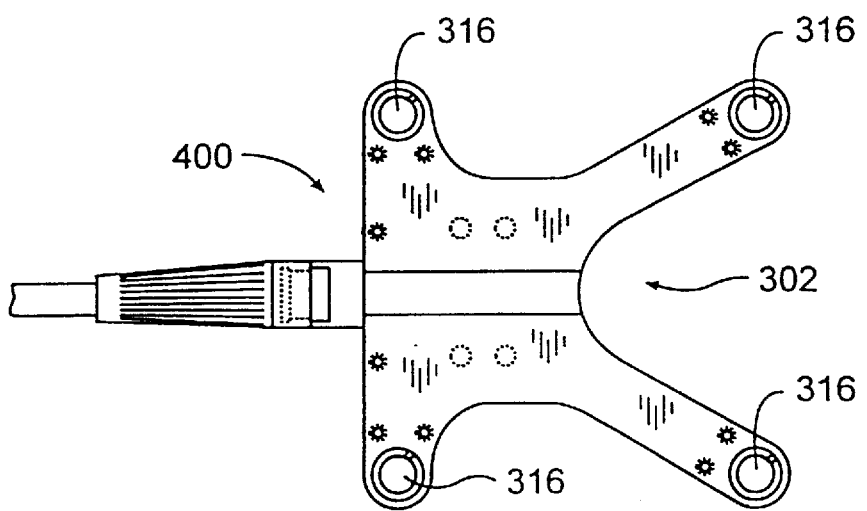
FIG. 13F is a top plan view of one preferred embodiment of a drill yoke localization frame according to the invention.
Figure 13G:
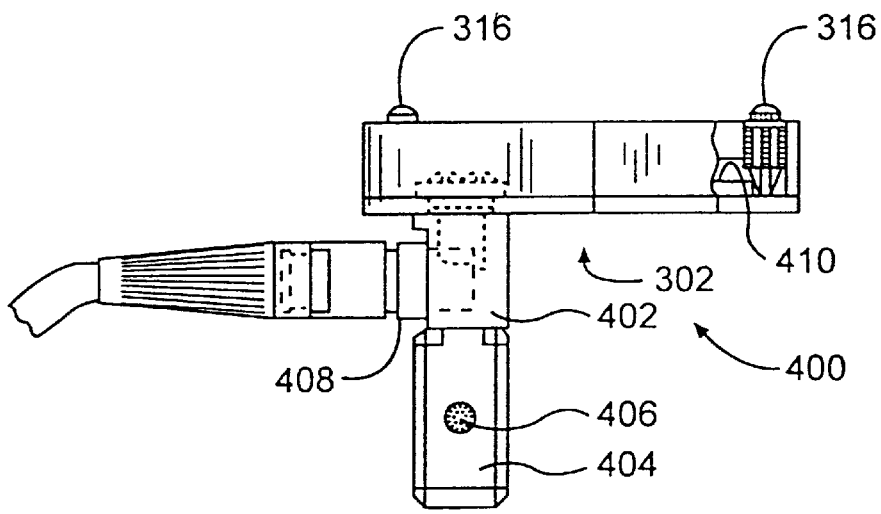
FIG. 13G is a side plan view, partially in cross section, of one preferred embodiment of a drill yoke localization frame according to the invention.

FIGS. 13F and 13G illustrate another localization device in the form of a drill yoke localization frame 400. This frame 400 includes a localization frame 302 of the same configuration as the localization frames for the localization biopsy guide frame 300 and the localization drill guide assembly 350. Projecting from the underside of the base plate 310 is a support member 402 which also supports a drill yoke 404 in a plane which is essentially perpendicular to the plane defined by the localization frame 302. Yoke 404 is essentially a collar which fits over the housing of a Rex drill and is fixedly attached thereto by a set screw 406. The drill yoke localization frame 400 allows the drill housing to be precisely positioned for use during surgery.

Figure 13J:
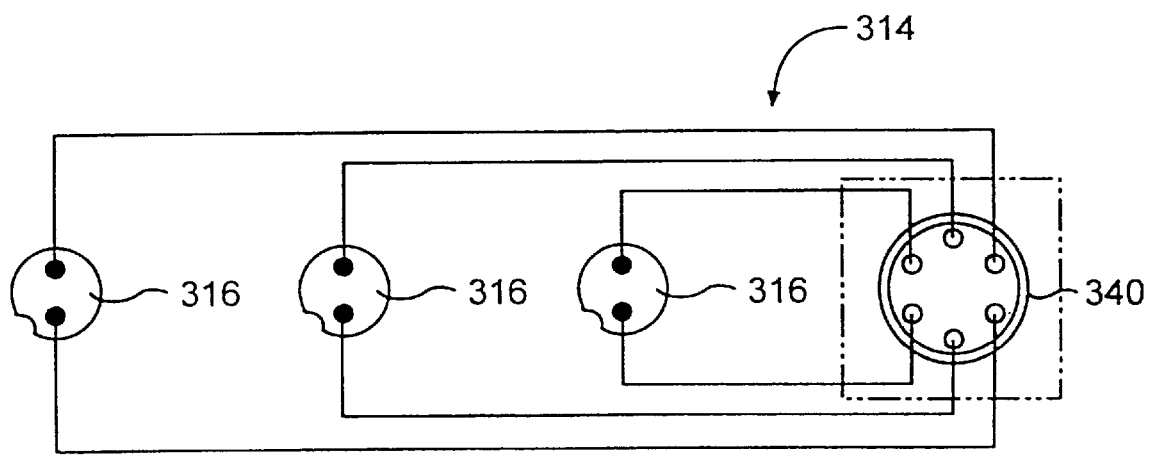
FIG. 13J is a wiring diagram of one preferred embodiment of a localization frame according to the invention.

Support member 402 also supports a connector 408 for receiving a cable which is connected to the digitizer control unit 114. Support member 402 has a hollow channel therein so that the connector 408 may be connected to the wires 410 which connect to the LEDs 316. FIG. 13J illustrates one preferred embodiment of a wiring connection between the LEDs 316 and the connector 408.

FIGS. 13H and 13I illustrate another localization device in the form of a ventriculostomy probe 500. Probe 500 includes a handle 502 having a bore 504 therein for receiving a support shaft 506 which in turn supports a catheter guide tube 508 along an axis which is parallel to the axis of the handle 502. The handle includes three LEDs 510 mounted along its top surface for communication with the camera array 110. The handle 502 has a hollow channel terminating in a bore 512 for receiving a connector 514. The connector 514 is connected to wires 516 which are also connected to the terminals of the LEDs 510. FIG. 13J illustrates one preferred embodiment of a wiring diagram for interconnecting the connector 514 and the LEDs 510. In operation, the tube 508 is positioned within the body, the brain for example, so that a catheter may be inserted within the body. Tube 508 includes a top slot 518 which allows a catheter to be inserted therein. Preferably, the tube tip at its center is collinear with the chip height of all three LEDs 510 so that a linear axis is defined therebetween. Based on this linear axis and the predetermined knowledge of the distance between the tip and the LEDs 510, the camera array 110 and digitizer 114 can determine the position of the tip at any instant during a surgical or medical procedure.

The system of the invention may be used in the following manner. A reference frame is attached to a body part. For example, cranial reference arc frame 122 may be attached directly to a head via a head clamp such as a Mayfield clamp or spine reference arc frame 200 may be attached directly to a spinous bone via thoraco-lumbar mount 212. Thereafter, movement of the body part will result in corresponding movement of the attached reference frame. The position of the body part may be tracked by energizing the LEDs of the reference frame to provide a signal to the camera array 110 so that the array can determine and track the position of the reference frame and, consequently, the position of the body part.

A localization frame is used to precisely position an instrument relative to the body part. For example, a localization biopsy guide frame 300 may be used to position a biopsy needle relative to the body part. Alternatively, a localization drill guide assembly 350 may be used to position a drill bit relative to the body part. Alternatively, a drill yoke localization frame 400 may be used to position a drill relative to the body part. Alternatively, a ventriculostomy probe 500 may be used to position a catheter relative to a body part. The position of the instrument may be tracked by energizing the LEDs of the localization frame to provide a signal to the camera array 110 so that the array can determine and track the position of the localization frame and, consequently, the position of the instrument.

During calibration of the system, the position of the reference frame relative to the body part is determined. Markers used during the preoperative scan are located and identified in coordinates of the surgical space as defined by the reference frame. Note that anatomic landmarks may be used as markers. This provides a relationship between the preoperative scan space and the surgical space. Once this relationship is established, the system knows the position of the preoperative scans relative to the reference frame and thus can generate scans which illustrate the position of the localization frame and the instrument relative to the body part. In other words, the system accomplishes image guided surgery. The system is ideally suited for locating small, deep-seated vascular lesions and tumors and for reducing the extent of the microsurgical dissection. It is also useful in identifying boundaries. For example, suppose a surgeon is trying to identify a boundary between normal brain and large supratentorial gliomas, which may be clearly shown on the preoperative scans but which may be difficult to visually locate in the operating room during a procedure. The surgeon would take a localization probe and position it a point near the boundary. The LEDs of the reference frame and localization probe are fired by use of the foot switch 116. As a result, the monitor 106 would provide a screen showing the position of the probe relative to a preoperative scan. By referring to the monitor, the surgeon can now determine the direction in which the probe should be more to more precisely locate the boundary. One the boundary is located, microcottonoid markers can be placed at the boundary of the tumor as displayed on the monitor before resection is started. The placement of ventricular catheters for shunts, ventriculostomy, or reservoirs is also facilitated by the use of the system, especially in patients who have small ventricles or who have underlying coagulopathy (e.g., liver failure, acquired immunodeficiency syndrome) that makes a single pass desirable. The system can also be useful for performing stereotactic biopsies. For further information regarding the system, see the following articles which are incorporated herein by reference in their entirety:

Germano, Isabelle M., The NeuroStation System for Image-Guided, Frameless Stereotaxy, *Neurosurgery*, Vol. 37, No. 2, August 1995.

Smith et al., The Neurostation™—A Highly accurate, Minimally Invasive Solution to Frameless Stereotactic Neurosurgery, *Computerized Medical Imaging and Graphics*, Vol. 18, No. 4, pp. 247–256, 1994.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

In view of the above, it will be seen that the several objects of the invention are achieved and other advantageous results attained.

As various changes could be made in the above without departing from the scope of the invention, it is intended that all matter contained in the above description and shown in the accompanying drawings shall be interpreted as illustrative and not in a limiting sense.

What is claimed is:

1. A system for use during a medical or surgical procedure on a body, said system generating a display from an image data set representing the position of one or more body elements during the procedure based on scans taken of the body by a scanner prior to the procedure, the scan having reference points for each of the one or more body elements, the reference points of a particular body element having a known spatial relation to the particular body element, said system comprising:

means for identifying, during the procedure, the position of the reference points for each of the one or more body elements to be displayed;

means for substantially discriminating the one or more body elements of the image data set by creating an image data subset defining each of the one or more body elements;

a processor modifying the image data subset according to the identified position of the reference points during the procedure, as identified by the identifying means, said processor generating a displaced image data set representing the position and geometry of the one or more body elements during the procedure; and a display utilizing the displaced image data set generated by the processor, illustrating the position and geometry of the one or more body elements during the procedure.

2. The system of claim 1 wherein the reference points are defined in relation to the one or more body elements and further comprising:

a device including one of a medical instrument, surgical instrument, probe and radiation delivery system; and means for identifying, during the procedure, the position of the device relative to one or more of the one or more body elements, wherein the display illustrates the relative position of the one or more body elements relative to the device during the procedure, and wherein the reference frame includes sensors and the reference array is attached to one of the one or more body elements and includes emitters communicating with the sensors of the reference frame to indicate the position of the reference frame relative to the reference array.

3. The system of claim 2 wherein the device position identifying means determines an orientation of the device relative to the one or more body elements and wherein the display illustrates the orientation of the device relative to the one or more body elements.

4. The system of claim 2 wherein the processor monitors the position of the device and deactivates it when the monitored position indicates that it is outside a predefined safe zone.

5. The system of claim 2 further comprising robotics to control the position of the device and wherein the processor would monitor the position of the instrument and instruct the robotics to control it in a predetermined manner.

6. The system of claim 1 wherein the identifying means comprises:

a reference array having a location outside the body for providing a reference; and means for determining the position of the reference points for the one or more body elements to be displayed relative to the reference array.

7. The system of claim 6 further comprising a registration probe in communication with the reference array and wherein the determining means is adapted to determine the position of a tip of the registration probe relative to the reference array, and the position of the reference points for the one or more body elements can be determined by positioning the tip of the registration probe at each of the reference points.

8. The system of claim 7 wherein the reference array includes sensors and wherein the registration probe includes emitters communicating with the sensors of the reference array to indicate the position of the registration probe relative to the reference array.

9. The system of claim 7 wherein the registration probe includes sensors and wherein the reference array includes emitters communicating with the sensors of the registration probe to indicate the position of the registration probe relative to the reference array.

10. The system of claim 6 further comprising a reference frame having a position in known relation to one of the one or more body elements, said reference frame in communication with the reference array, and further comprising means for determining the position of the reference frame relative to the reference array, the body being movable during the procedure while the one or more body elements remain in fixed relation to each other and in known relation to the reference frame so that the system can determine the position of each of the one or more body elements after movement without again identifying the relative position of each of the reference points for each of the one or more body elements.

11. The system of claim 10 wherein the reference array includes sensors and wherein the reference frame is capable of one of continuously and periodically detecting and tracking at least one of the one or more body elements and includes emitters communicating with the sensors of the reference array to indicate the position of the reference frame relative to the reference array.

12. The system of claim 1 wherein the processor translates each of the image data subsets from the position of the one or more body elements prior to the procedure to the position of the one or more body elements during the procedure, and the displaced data set consists of the translated image data subsets.

13. The system of claim 1 wherein the identifying means comprises a device for determining a position of a contour of each of the one or more body elements during the procedure and wherein the processor compares the position of the contour of each of the one or more body elements during the procedure as determined by the device to the position of the contour of each of the one or more body elements prior to the procedure as represented by the image data sub-set.

14. The system of claim 13 wherein the identifying means comprises an ultrasound probe for determining a position of a contour of each of the one or more body elements during the procedure and wherein the processor compares the position of the contour of the each of the one or more body elements during the procedure as determined by the device to the position of the contour of each of the one or more body elements prior to the procedure as represented by the image data subset, and the contour of the one or more body elements may be determined without the need for exposing the one or more body elements.

15. The system of claim 14 wherein said reference array has emitters thereon in communication with the ultrasound probe, and the determining means is adapted to determine the position of the ultrasound probe relative to the reference array, and the position of the contour of each of the one or more body elements can be determined.

16. The system of claim 14 wherein said ultrasound probe has emitters thereon in communication with the reference array, and the determining means is adapted to determine the position of the ultrasound probe relative to the reference array, and the position of the contour of each of the one or more body elements can be determined.

17. The system of claim 13 wherein the identifying means comprises a scanner for determining a position of a contour of each of the one or more body elements during the procedure and wherein the processor compares the position of the contour of the each of the one or more body elements during the procedure as determined by the device to the position of the contour of each of the one or more body elements prior to the procedure as represented by the image data subset.

18. The system of claim 17 wherein said scanner has emitters thereon in communication with the reference array, and the determining means is adapted to determine the position of the scanner relative to the reference array, and the position of the contour of each of the one or more body elements can be determined.

19. The system of claim 17 wherein said reference array has emitters thereon in communication with the scanner, and the determining means is adapted to determine the position of the scanner relative to the reference array, and the position of the contour of each of the one or more body elements can be determined.

20. The system of claim 1 wherein the processor transforms each of the image data subsets representing the position and shape of the one or more body elements prior to the procedure to represent the position and shape of the one or more body elements during the procedure, and the displaced data set consists of the transformed image data subsets.

21. A system for use during a medical or surgical procedure on a body, said system generating a display representing the position of plural body elements during the procedure based on scans taken of the body by a scanner prior to the procedure, the scan having reference points for each of the body elements, the reference points of a particular body element having a known spatial relation to the particular body element, said system comprising:

means for identifying, during the procedure, the position of the reference points for each of the body elements to be displayed, the identifying means comprising a reference array having a location outside the body for providing a reference and means for determining the position of the reference points for the body elements to be displayed relative to the reference array;

a processor modifying the image data set according to the identified position of the reference points during the procedure, as identified by the identifying means, said processor generating a displaced image data set representing the position and geometry of the body elements during the procedure;

a display utilizing the displaced image data set generated by the processor, illustrating the position and geometry of the body elements during the procedure; and a reference frame having a position in known relation to one of the body elements, said reference frame in communication with the reference array, and further comprising means for determining the position of the reference frame relative to the reference array, the body being movable during the procedure while the body elements remain in fixed relation to each other and in known relation to the reference frame so that the system can determine the position of each of the body elements after movement without again identifying the relative position of each of the reference points for each of the body elements, wherein the reference array includes sensors and wherein the reference frame is attached to one of the body elements and includes emitters communicating with the sensors of the reference array to indicate the position of the reference frame relative to the reference array.

22. A system for use during a medical or surgical procedure on a body, said system generating a display representing the position of body elements during the procedure based on scans taken of the body by a scanner prior to the procedure, the scan having reference points for each of the body elements, the reference points of a particular body element having a known spatial relation to the particular body element, said system comprising:

means for identifying, during the procedure, the position of the reference points for each of the body elements to be displayed, the identifying means comprising a reference array having a location outside the body for providing a reference and means for determining the position of the reference points for the body elements to be displayed relative to the reference array;

a processor modifying the image data set according to the identified position of the reference points during the procedure, as identified by the identifying means, said processor generating a displaced image data set representing the position and geometry of the body elements during the procedure;

a display utilizing the displaced image data set generated by the processor, illustrating the position and geometry of the body elements during the procedure; and a reference frame having a position in known relation to one of the body elements, said reference frame in communication with the reference array, and further comprising means for determining the position of the reference frame relative to the reference array, the body being movable during the procedure while the body elements remain in fixed relation to each other and in known relation to the reference frame so that the system can determine the position of each of the body elements after movement without again identifying the relative position of each of the reference points for each of the body elements, wherein the reference frame includes sensors and wherein the reference array is attached to one of the body elements and includes emitters communicating with the sensors of the reference frame to indicate the position of the reference frame relative to the reference array.

23. A method for use during a procedure, said method generating a display representing the position of body elements during the procedure based on an image data set generated prior to the procedure, which image data set has reference points for each of the body elements, said method comprising the steps of:

identifying, during the procedure, the relative position of each of the reference points for each of the body elements to be displayed;

modifying the image data set according to the identified relative position of each of the reference points during the procedure in order to generate a displaced image data set representing the position of the body elements during the procedure;

generating a display based on the displaced image data set illustrating the relative position of the body elements during the procedure;

providing a reference frame having a position in fixed relation to one of the body elements, said reference frame in communication with the reference array; and determining the position of the reference frame relative to the reference array, the body being movable during the procedure while the body elements remain in fixed relation to each other and the reference frame so that the method can determine the position of each of the body elements after movement without again identifying the relative position of each of the reference points for each of the body elements.

24. The method of claim 23 further comprising the step of repositioning the body elements so that the display based on the displaced data set representing the position of the body elements during the procedure is substantially the same as the display based on the image data set generated prior to the procedure, the position of the body elements after repositioning being substantially the same as the position of the body elements prior to the procedure when the image data set was generated.

25. The method of claim 23 further comprising the steps of:

providing a reference array having a location outside the body for providing a reference; and determining the position of the reference points of the body elements to be displayed relative to the reference array.

26. The method of claim 25 further comprising the steps of providing a registration probe in communication with the reference array and determining the position of the reference points of the body elements by positioning the tip of the registration probe at each of the reference points.

27. The method of claim 23 further comprising the step of discriminating the body elements of the image data set by creating an image data subset defining each of the body elements.

28. The method of claim 27 further comprising the step of translating each of the image data subsets from the position of the body elements prior to the procedure to the position of the body elements during the procedure, the displaced data set comprising the translated image data subsets.

29. The method of claim 27 comprising the steps of determining a position of a contour of each of the body elements during the procedure and comparing the position of the contour of the each of the body elements during the procedure to the position of the contour of each of the body elements prior to the procedure as represented by the image data set.

30. The method of claim 23 wherein the identifying step comprises the steps of positioning the body elements between a fluoroscopic tube and a fluoroscope plate in fixed relation to the tube, energizing the tube to generate a projection of each of the elements on the plate, determining the relative position of the fluoroscopic projection of each of the body elements during the procedure and comparing the position represented by the fluoroscopic projection of each of the body elements during the procedure to the relative position of the body elements prior to the procedure.

31. A system for use during a medical or surgical procedure on a body, the system generating a display from an image data set representing the position of at least one body element during the procedure based on scans taken of the body by a scanner prior to the procedure, the scan having reference points for the at least one body element, the reference points of a particular body element having a known spatial relation to the particular body element, the system comprising:

an identifying system configured to identify, during the procedure, the position of the reference points for the at least one body element to be displayed;

a processor configured to substantially discriminate the at least one body element of the image data set by creating an image data subset defining the at least one body element;

a processor programmed to modify the image data subset according to the identified position of the reference points during the procedure, as identified by the identifying system, the processor generating a displaced image data set representing the position and geometry of the at least one body element during the procedure; and a display utilizing the displaced image data set generated by the processor to illustrate the position and geometry of the at least one body element during the procedure.

32. The system of claim 31, wherein the reference points are defined in relation to the at least one body element and further comprising:

an instrument including one of a medical instrument, surgical instrument, probe and radiation delivery system; and an instrument position identifying system for identifying, during the procedure, the position of the instrument relative to the at least one body element, wherein the instrument position identifying system determines an orientation of the instrument relative to the at least one body element and the display illustrates the orientation of the instrument relative to the at least one body element during the procedure, and wherein the reference frame includes sensors and the reference array is attached to a body element and includes emitters communicating with the sensors of the reference frame to indicate the position of the reference frame relative to the reference array.

33. The system of claim 32, further comprising robotics to control the position of the instrument and wherein the processor monitors the position of the instrument and instruct the robotics to control it in a predetermined manner.

34. The system of claim 32, wherein the processor monitors the position of the instrument and deactivates it when the monitored position indicates that it is outside a predefined safe zone.

35. The system of claim 31, wherein the identifying system comprises a reference array located outside the body for providing a reference and a registration probe in communication with the reference array, the processor determining the position of a tip of the registration probe relative to the reference array, wherein the position of the reference points for the at least one body element relative to the reference array can be determined by positioning the tip of the registration probe at each of the reference points.

36. The system of claim 35, wherein the reference array includes sensors and the registration probe includes emitters communicating with the sensors of the reference array to indicate the position of the registration probe relative to the reference array.

37. The system of claim 35, wherein the registration probe includes sensors and the reference array includes emitters communicating with the sensors of the registration probe to indicate the position of the registration probe relative to the reference array.

38. The system of claim 35, wherein the reference array includes sensors, and further comprising a reference frame having a position in known relation to the at least one body element, the reference frame including emitters communicating with the sensors of the reference array to indicate the position of the reference frame relative to the reference array, the body being movable during the procedure while the at least one body element remains in known relation to the reference frame so that the system can determine the position of the at least one body element after movement without again identifying the relative position of each of the reference points for the at least one body element.

39. The system of claim 31, wherein the processor translates the image data subset from the position of the at least one body element prior to the procedure to the position of the at least one body element during the procedure, and the displaced data set consists of the translated image data subsets.

40. The system of claim 31, wherein the identifying system comprises a device for determining a position of a contour of the at least one body element during the procedure and wherein the processor compares the position of the contour of the at least one body element during the procedure to the position of the contour of the at least one body element prior to the procedure as represented by the image data subset.

41. The system of claim 40, wherein the identifying system comprises an ultrasound probe for determining a position of a contour of the at least one body element during the procedure and wherein the processor compares the position of the contour of the at least one body element during the procedure to the position of the contour of the at least one body element prior to the procedure as represented by the image data subset, and the contour of the at least one body element may be determined without the need for exposing the at least one body element.

42. The system of claim 41, wherein the reference array has emitters thereon in communication with the ultrasound probe, and the processor determines the position of the ultrasound probe relative to the reference array for determining the position of the contour of the at least one body element.

43. The system of claim 41, wherein the ultrasound probe has emitters thereon in communication with the reference array, and the processor determines the position of the ultrasound probe relative to the reference array for determining the position of the contour of the at least one body element.

44. The system of claim 40, wherein the identifying system comprises a scanner for determining a position of a contour of the at least one body element during the procedure and wherein the processor compares the position of the contour of the at least one body element during the procedure to the position of the contour of the at least one body element prior to the procedure as represented by the image data subset.

45. The system of claim 44, wherein the scanner has emitters thereon in communication with the reference array, and the processor determines the position of the scanner relative to the reference array for determining the position of the contour of the at least one body element.

46. The system of claim 44, wherein the reference array has emitters thereon in communication with the scanner, and the processor determines the position of the scanner relative to the reference array for determining the position of the contour of the at least one body element.

* * * * *